United States Patent
Dohi et al.

(10) Patent No.: US 7,731,990 B2
(45) Date of Patent: *Jun. 8, 2010

(54) POWDERY COMPOSITION FOR NASAL ADMINISTRATION

(75) Inventors: Masahiko Dohi, Hino (JP); Yoshihisa Nishibe, Hino (JP); Yuji Makino, Tokyo (JP); Tako Fujii, Hino (JP)

(73) Assignee: Teijin Limited, Osaka (JP)

( * ) Notice: Subject to any disclaimer, the term of this patent is extended or adjusted under 35 U.S.C. 154(b) by 1190 days.

This patent is subject to a terminal disclaimer.

(21) Appl. No.: 10/860,058

(22) Filed: Jun. 4, 2004

(65) Prior Publication Data

US 2004/0219108 A1    Nov. 4, 2004

Related U.S. Application Data (63) Continuation of application No. 09/125,814, filed on Aug. 26, 1998, now Pat. No. 6,881,423.

(30) Foreign Application Priority Data

Feb. 27, 1996  (JP) .................................... 8-39553
Feb. 28, 1996  (JP) .................................... 8-41079

(51) Int. Cl.
A61K 9/50      (2006.01)
A61K 9/14      (2006.01)

(52) U.S. Cl. ................................... 424/499; 424/489
(58) Field of Classification Search ................. 424/499, 424/489
See application file for complete search history.

(56) References Cited

U.S. PATENT DOCUMENTS

| | | | |
|---|---|---|---|
| 4,294,829 A | 10/1981 | Suzuki et al. | |
| 4,613,500 A | 9/1986 | Suzuki et al. | |
| 4,835,142 A | 5/1989 | Suzuki et al. | |
| 5,578,324 A | 11/1996 | Dohi et al. | |
| 5,626,871 A | 5/1997 | Makino et al. | |
| 6,881,423 B2* | 4/2005 | Dohi et al. | 424/499 |

FOREIGN PATENT DOCUMENTS

EP       0 187 433       7/1986

(Continued)

OTHER PUBLICATIONS

Hormone Metabolic Research, vol. 22, 1990, pp. 170-174, "Biological Activity of Nasally Administered Insulin in Normal Subjects", Martha S. Nolte et al.
Diabetic Medicine, vol. 8, p. 366-370, 1991, "Meal-time Intranasal Insulin Delivery in Type 2 Diabetes", D.G. Bruce et al.
Makino, Y., et al., Pharmaceutical Research (vol. 12, No. 9, Suppl., S-313, 1995).
Kirk-Othmer, Encyclopedia of Chemical Technology, 2005, "Particle Size Measurement".

(Continued)

*Primary Examiner*—Shengjun Wang
(74) *Attorney, Agent, or Firm*—Sughrue Mion, PLLC (57) ABSTRACT

A powdery composition for nasal administration, where
(1) the composition contains (i) a drug, (ii) a water-absorbing and gel-forming base material such as hydroxypropyl cellulose or hydroxypropylmethyl cellulose and (iii) a water-absorbing and water-insoluble base material such as crystalline cellulose or α-cellulose,
(2) wherein the amount of the water-absorbing and gel-forming base material is about 5-40 wt % based on the total of the water-absorbing and gel-forming base material and the water-absorbing and water-insoluble base material, and
(3) wherein the drug is unevenly dispersed more on/in the water-absorbing and water-insoluble base material than on/in the water-absorbing and gel-forming base material.

22 Claims, 1 Drawing Sheet

FOREIGN PATENT DOCUMENTS

| | | |
|---|---|---|
| EP | 0 571 671 A1 | 12/1993 |
| GB | 2193891 A | 2/1988 |
| JP | 57-32215 A | 2/1982 |
| JP | 59-163313 | 9/1984 |
| JP | 57-032215 | 2/1985 |
| JP | 85-034925 | 8/1985 |
| JP | 60-224616 | 9/1985 |
| JP | 60-224616 A | 11/1985 |
| JP | 93-24149 | 12/1993 |
| JP | 7-242550 A | 9/1995 |

OTHER PUBLICATIONS

Ullmann's Encyclopedia of Industrial Chemistry, 2002, "Particle Size Analysis and Characterization of a Classification Process".

Dr. Alan Rawle, "The Importance of Particle Size Analysis in the Pharmaceutical Industry" (date unknown).

Ainley Wade and Paul J. Weller, "Handbook of Pharmaceutical Excipients", 1994.

M. Dohi et al., Proceed. Intern. Symp. Control. Rel. Bioact. Mater., 23 (1996), 483-484, "The Enhanced Nasal Absorption of Peptides Using Powder Preparations with Mixed Base Materials".

* cited by examiner

POWDERY COMPOSITION FOR NASAL ADMINISTRATION

This application is a continuation of application Ser. No. 09/125,814 filed Aug. 26, 1998 now U.S. Pat. No. 6,881,423, which is a national stage application of PCT/JP97/00541 filed Feb. 26, 1997; the disclosures of which is incorporated herein by reference.

TECHNICAL FIELD

The present invention relates to a powdery composition for nasal administration, in which the absorption of a drug through the nasal mucosa is improved. More specifically, the present invention provides a powdery composition for nasal administration which can exhibit a high maximum blood concentration by compounding a pair of base materials of specific kinds and having a specific composition to specify the state of the existence of the drug in the base materials.

BACKGROUND ARTS

For instance, in a non-peptide/non-proteinaceous drug such as an anti-inflammatory steroid, the development of a pharmaceutical preparation for nasal administration is desired because of the fact that (1) the topical nasal mucosa can be an objective site of action, (2) rapid action can be expected in the pharmaceutical preparation for nasal administration, (3) on the other hand, the absorption through oral administration is low in some drug, and others.

Further, many of peptide/proteinaceous drugs are not readily absorbed into body mainly because it is readily decomposed by proteolytic enzymes in the gastrointestinal tract when orally administered. Therefore, it is often forced to administer such a drug by injection in order to use it for therapy. Unfortunately, injection imposes burden such as pain, attendance to the hospital, etc., to a patient. Accordingly, it is desired to develop a pharmaceutical preparation for non-invasive administration such as nasal administration which can substitute injection.

Nasal administration, by which a drug is transferred into circulating blood through the nasal mucosa, is being energetically studied as a method for non-injection type administration together with transdermal administration, transocular administration, transrectal administration, transpulmonary administration, etc. Among these non-injection type administration methods, the nasal administration is easy to administer a drug. Moreover, nasal administration is considered to be superior in the absorption of a drug among the non-injection type administration methods since the blood vessel system in the nasal mucous membrane is more developed compared with the skin, the ocular mucous membrane, the rectal mucous membrane, etc. Therefore, a pharmaceutical preparation for nasal administration has been put into practice in some drugs. Further, the transfer of a drug into blood in nasal administration is faster than that in oral administration, and it can be expected that nasal administration has immediate effect similar to injection. On the other hand, the absorption of a drug through the nasal mucosa depends on physical properties such as lipophilicity of the drug and also on the molecular weight, etc. It is pointed out that a drug having a high solubility in water, a drug having a high lipophilicity, a peptide/proteinaceous drug having a large molecular weight, etc., is generally low in absorption trough the nasal mucosa. Under these circumstances, some contrivances to improve the absorption of such a drug through the nasal mucosa has been proposed.

For instance, Suzuki, et al., [Japanese Patent Publication (Examined) 60(1985)-34925] disclosed a long acting pharmaceutical preparation for nasal cavity comprising a cellulose ether and a drug.

The long acting pharmaceutical preparation for nasal cavity of the patent publication is aimed to allow a drug to adhere on the nasal mucosa and to slowly release the drug over a long period of time. Some of the objects, i.e. the drug is absorbed through the nasal mucosa and the effective amount of the drug is released in a sustained state, have been achieved. However, the main object of a long acting pharmaceutical preparation of said patent is put on the slow releasing of the drug, and accordingly the enhancement of absorption of the drug appears to be not always sufficient. The drugs concretely cited as preferable examples in said patent include an anti-inflammatory steroid, an analgesic anti-inflammatory agent, an anti-histaminic agent, a drug having anti-allergic effect, etc., for which the keeping of topical concentration rather than systemic absorption is important.

In a long acting pharmaceutical preparation for nasal cavity of said patent publication, it is assumed that a high pernasal absorption ratio is hardly achieved for a drug having a high solubility in water, a drug having a high lipophilicity or a peptide/proteinaceous drug having a large molecular weight. Under these circumstances, the development of a pharmaceutical preparation for administering such a drug on the nasal mucosa, which can utilize it effectively in terms of curing effect and curing efficiency, is strongly desired.

Nolte, et al., (Hormone Metabolic Research Vol. 22, 170-174, 1990) and Bruice et al., (Diabetic Medicine Vol. 8, 366-370, 1991) reported insulin preparations for nasal administration containing sodium glycolate or sodium taurofusidate as an absorption promoter. However, these absorption promoters have problems in irritation on the nasal mucosa, and the preparations have not been put in practice yet.

On the other hand, Suzuki, et al., [Japanese Patent Publication (Examined), 62(1987)-42888] disclosed a powdery composition for nasal administration excellent in absorption through the nasal mucosa comprising a polypeptide and a water-absorbing and water-insoluble base material. They reported that the nasal absorption of the polypeptide without using an absorption promoter had been achieved in the composition.

However, even in the composition of the above patent publication, none of the nasal absorption ratios of polypeptides [the area under blood concentration-time curve (AUC) after nasal administration] exceeds 10-20% of AUC in injection. For instance, in Example 4 of the patent publication, the maximum blood concentration of insulin was less than 200 µU/ml when 10 units of insulin had been administered to a rabbit, and it was about 20% of the maximum blood concentration obtained in injection with same amount of insulin. The absorption ratio of the nasal preparation determined from AUC is estimated to be less than 10% of the absorption ratio of injection.

The patent publication describes the combined use of a water-absorbing and water-insoluble base material with a water-absorbing and water-soluble base material in an amount of 0.1-60 wt % based on the water-absorbing and water-insoluble base material, especially preferably 1-50 wt %.

However, concerning the objects and the effects of the combined use, only the slow releasing effect (slow releasability or sustainability) comparing the single use of a water-absorbing and water-insoluble base material is described.

Further, there is no description about the use of a non-peptide/non-proteinaceous drug instead of a polypeptide.

Furthermore, in spite that the patent publication cites a number of water-absorbing and water-insoluble base materials including crystalline cellulose and a number of water-absorbing and water-soluble base materials including hydroxypropyl cellulose, it does not mention at all that a combination of base materials having specific kinds, specific compositions and specific particle sizes among these base materials can provide a powdery composition for nasal administration which can exhibit an excellent maximum blood concentration for a peptide/proteinaceous drug or a non-peptide/non-proteinaceous drug.

Generally, a peptide/proteinaceous drug is expensive, and further when an absorbing ratio is low, its blood concentration tends to vary largely and an expected curing effect is not stably obtained in many cases. Therefore, it is desired to provide a composition of a peptide/proteinaceous drug for nasal administration capable of giving a higher rate of absorption. Further, it is strongly desired to provide a composition for nasal administration which is safe and capable of giving a higher rate of absorption at the same time. Furthermore, it is desired to provide a composition for nasal administration capable of giving a higher maximum blood concentration. The situations are same in a non-peptide/non-proteinaceous drug.

One of the objects of the present invention is to provide a composition for nasal administration excellent in absorption of a drug.

Another object of the present invention is to provide a composition for nasal administration capable of exhibiting high absorption of a drug, especially a higher maximum blood concentration.

A further object of the present invention is to provide a composition for nasal administration capable of exhibiting high absorption, especially a higher maximum blood concentration, even for a drug having a high water solubility, a drug having a high lipophilicity or a peptide/proteinaceous drug having a larger molecular weight.

Still another object of the present invention is to provide a composition for nasal administration capable of exhibiting more excellent absorption, especially capable of exhibiting a higher maximum blood concentration, also for a drug which can exhibit excellent nasal absorption by nature, that is, a drug which is not high in water solubility nor high in lipophilicity, a drug which is a non-peptide/non-proteinaceous drug, etc.

Yet another object of the present invention is to provide a composition for nasal administration which is described in the above objects and at the same time excellent in safety.

The inventors of the present invention have zealously pursued studies for achieving the above-mentioned tasks and completed the present invention by finding that one can provide a new powdery composition for nasal administration excellent in absorption through the nasal mucosa by using a pair of base materials of specific kinds and having a specific composition and by specifying the state of existence of a main drug in the base materials, even for the drug having low absorption through the nasal mucosa or a non-peptide/non-proteinaceous drug.

DISCLOSURE OF THE INVENTION

The present invention is a powdery composition for nasal administration, which is characterized in that (1) the composition contains (i) a drug, (ii) a water-absorbing and gel-forming base material of one kind or more selected from the group comprising hydroxypropyl cellulose, hydroxypropylmethyl cellulose, methyl cellulose, hydroxyethyl cellulose and sodium carboxymethyl cellulose and (iii) a water-absorbing and water-insoluble base material of one kind or more selected from the group comprising crystalline cellulose, α-cellulose, cross-linked sodium carboxy-methyl cellulose, cross-linked starch, gelatin, casein, tragacanth gum, polyvinyl pyrrolidone, chitin and chitosan, (2) the content of the water-soluble and gel-forming base material is about 5-40 wt % based on the total of the water-absorbing and water-insoluble base material and the water-absorbing and gel-forming base material, and (3) the drug is unevenly dispersed more on/in the water-absorbing and water-insoluble base material than on/in the water-absorbing and gel-forming base material.

BEST MODE FOR CARRYING OUT THE INVENTION

Preferred examples of a drug of the present invention include non-peptide/non-proteinaceous drugs and peptide/proteinaceous drugs.

A variety of non-peptide/non-proteinaceous drugs are usable as the non-peptide/non-proteinaceous drug of the present invention. The concrete examples of the non-peptide/non-proteinaceous drug include anti-inflammatory steroids or nonsteroidal anti-inflammatory drugs, analgesic anti-inflammatory agents, sedatives, treating agents for depression, antitussive expectorants, antihistaminic agents, antiallergic drugs, antiemetic drugs, hypnotics, vitamin preparations, sex steroid hormones, antineoplastic drugs, antiarrhythmic drugs, antihypertensive drugs, antianxiety drugs, psychotropic drugs, antiulcer drugs, cardiotonics, analgesics, bronchodilators, treating agents for obesity, antithrombotic drugs, antidiabetic drugs, muscle relaxants, anti-rheumatics, etc. One kind or more selected from the group comprising the above drugs can be used as the non-peptide/non-proteinaceous drug. Among them, one kind or more selected from the group comprising antiemetic drugs, hypnotics, vitamin preparations, sex steroid hormones and analgesics are preferable.

Precisely, examples of the non-peptide/non-proteinaceous drug include one kind or more selected from the group comprising the followings: anti-inflammatory steroids or nonsteroidal anti-inflammatory drugs such as hydrocortisone, prednisolone, triamcinolone, dexamethasone, betamethasone, beclometasone, fluticasone, mometasone, fluocortin, budesonide, salbutamol and salmeterol; analgesic anti-inflammatory agents such as acetaminophen, phenacetin, aspirin, aminopyrine, sulpyrine, phenylbutazone, mefenamic acid, flufenamic acid, ibufenac, ibuprofen, alclofenac, diclofenac and indomethacin; sedatives such as scopolamine; treating agents for depression such as imipramine; antitussive expectorants such as sodium cromoglycate, codeine phosphate and isoproterenol hydrochloride; antihistaminic agents such as diphenhydramine, triprolidine, isothipendyl and chlorpheniramine; antiallergic drugs such as amlexanox, azelastine, ozagrel, tranilast and ketotifen; antiemetic drugs such as ondansetron, granisetron, metoclopramide, cisapride and domperidone; hypnotics such as brotizolam and melatonin; vitamin preparations such as cyanocobalamin and mecobalamin; sex steroid hormones such as estradiol, estriol, progesterone and testosterone; antineoplastic drugs such as tamoxifen and tegafur; antiarrhythmic drugs such as propranolol and atenolol; antihypertensive drugs such as nicardipine; antianxiety drugs such as diazepam; psychotropic drugs such as nitrazepam; antiulcer drugs such as cimetidine and ranitidine; cardiotonics such as dopamine; analgesics such as morphine and buprenorphine; bronchodilators such as oxitropium and ozagrel; treating agents for obesity such as mazindol; antithrombotic drugs such as beraprost and carbacyclin; antidiabetic drugs such as acarbose and sorbinil; muscle relaxants such as pinaverium and inaperisone; antirheumatics such as actarit and platonin; etc.

Further, a peptide/proteinaceous drug of the present invention preferably has a molecular weight of less than 30,000. The peptide/proteinaceous drug having a molecular weight of less than 30,000 is exemplified in the following: luteinizing hormone-releasing hormones, growth hormone-releasing factors, somatostatin derivatives, vasopressins, oxytocins, hirudin derivatives, enkephalins, adrenocorticotropic hormone derivatives, bradykinin derivatives, calcitonins, insulins, glucagon derivatives, growth hormones, growth hormone-releasing hormones, luteinizing hormones, insulin-like growth factors, calcitonin gene-related peptides, atrial natriuretic polypeptide derivatives, interferons, interleukins, erythropoietin, granulocyte colony forming-stimulating factor, macrophage forming-stimulating factor, parathyroid hormones, parathyroid hormone-releasing hormone, prolactin, thyroid-stimulating hormone-releasing hormone and angiotensins. As the peptide/proteinaceous drug of the present invention, one kind or more selected from the group comprising the substances shown above as concrete examples can be used.

A water-absorbing and gel-forming base material of the present invention is a base material of one kind or more selected from the group comprising hydroxypropyl cellulose, hydroxypropylmethyl cellulose, methyl cellulose, hydroxyethyl cellulose and sodium carboxymethyl cellulose.

Among these base materials, as the water-absorbing and gel-forming base material of the present invention, one kind or more selected from the group comprising hydroxypropyl cellulose, hydroxypropylmethyl cellulose, methyl cellulose and sodium carboxymethyl cellulose is preferable, and hydroxypropyl cellulose is especially preferable.

Further, as the hydroxypropyl cellulose, a hydroxypropyl cellulose having a viscosity of 2% aqueous solution in the range of 150-4000 cps is preferable. The viscosity means a kinetic viscosity and can be determined by a viscometer such as Cannon-Fenske viscometer, Cannon-Fenske reverse flow-type viscometer, Ubbellohde viscometer or Ostwald viscometer. Among them, an Ubbellohde viscometer is preferable since it gives high accuracy of measurement. The values of viscosity described in the present invention were determined at 37° C. using an Ubbellohde viscometer produced by Shibata Kagaku Kikai Kougaku Co. Although a hydroxypropyl cellulose having a lower viscosity is available, when a hydroxypropyl cellulose having a viscosity of lower than 150 cps is used, the increasing effect on maximum blood concentration of the present invention can not always be attained in a sufficient manner.

A water-absorbing and water-insoluble base material of the present invention is one kind or more selected from the group comprising crystalline cellulose, α-cellulose, cross-linked sodium carboxymethyl cellulose, cross-linked starch, gelatin, casein, tragacanth gum, polyvinyl pyrrolidone, chitin and chitosan.

Among them, as the water-absorbing and water-insoluble base material of the present invention, one kind or more selected from the group comprising crystalline cellulose, α-cellulose, cross-linked sodium carboxymethyl cellulose, cross-linked starch, gelatin, casein, tragacanth gum, polyvinyl pyrrolidone, chitin and chitosan is preferable, and crystalline cellulose is especially preferable.

Examples of a preferable combination of a water-absorbing and gel-forming base material and a water-absorbing and water-insoluble base material include a combination between both the base materials cited above as preferable examples. The combination of hydroxypropyl cellulose as the water-absorbing and gel-forming base material and crystalline cellulose as the water-absorbing and water-insoluble base material is especially preferable.

A water-absorbing and gel-forming base material in the present invention is used in an amount of about 5-40 wt % based on the total of the water-absorbing and water-insoluble base material and the water-absorbing and gel-forming base material.

The amount of the water-absorbing and gel-forming base material also depends on the kind of a drug of the present invention. In cases where the drug is a non-peptide/non-proteinaceous drug, the amount is preferably about 20-40 wt % since prominent increasing effect on maximum blood concentration is observed in this range.

In cases where a drug of the present invention is a peptide/proteinaceous drug, the range of the preferable amount of the water-absorbing and gel-forming base material is subdivided by the molecular weight of the drug. In cases where the molecular weight of the peptide/proteinaceous drug is not less than 500 and less than 1500, prominent increasing effect on maximum blood concentration is observed when the amount of the water-absorbing and gel-forming base material is in the range of about 5-30 wt %, and especially prominent effect is observed in the range of 20-30 wt %. Further, in cases where the molecular weight of the peptide/proteinaceous drug is not less than 1500 nor more than 30,000, prominent increasing effect on maximum blood concentration is observed when the amount of the water-absorbing and gel-forming base material is in the range of about 5-20 wt %, and especially prominent effect is observed in the range of 10-20 wt %.

Examples of the peptide/proteinaceous drug having a molecular weight of not less than 500 and less than 1500 include vasopressins, luteinizing hormone-releasing hormones, growth hormone-releasing factors, somatostatin derivatives, oxytocins, hirudin derivatives, enkephalins, adrenocorticotropic hormone derivatives, bradykinin derivatives, etc. Further, examples of the peptide/proteinaceous drug having a molecular weight of not less than 1500 and less than 30,000 include calcitonins, insulins, glucagon derivatives, growth hormones, growth hormone-releasing hormones, luteinizing hormones, insulin-like growth factors, calcitonin gene-related peptides, atrial natriuretic polypeptide derivatives, interferons, erythropoietin, granulocyte colony forming-stimulating factor, macrophage forming-stimulating factor, parathyroid hormones, parathyroid hormone-releasing hormone, prolactin, thyroid-stimulating hormone-releasing hormone, angiotensins, etc.

A powdery composition for nasal administration of the present invention is characterized in that a drug is unevenly dispersed more on/in a water-absorbing and water-insoluble base material than on/in a water-absorbing and gel-forming base material.

The state, in which the drug is unevenly dispersed more on/in the water-absorbing and water-insoluble base material than on/in the water-absorbing and gel-forming base material, includes a state in which the drug is adhered to base materials according to the compounding ratio of the base materials. A state, in which 70 wt % or more based on the drug is adhered to both the base materials according to the compounding ratio of the base materials, is preferable. A state, in which 80 wt % or more based on the drug is adhered to both the base materials according to the compounding ratio of the base materials, is especially preferable. For instance, in a state in which 70 wt % or more based on the drug is adhered to both the base materials according to their compounding ratio, when the amount of the water-absorbing and gel-forming base material is 40 wt % based on the total of both the base materials, 42 wt % based on the drug adheres to the water-absorbing and water-insoluble base material, 28 wt % adheres to the water-absorbing and gel-forming base material, and the remaining 30 wt % is homogeneously dispersed in the composition.

Furthermore, the state, in which the drug is unevenly dispersed more on/in the water-absorbing and water-insoluble base material than on/in the water-absorbing and gel-forming base material, also includes a state in which the drug is adhered to the water-absorbing and water-insoluble base material in a larger amount than in a state in which the drug is adhered to both the base materials according to their compounding ratio. A state, in which 60 wt % or more based on the drug is adhered to the water-absorbing and water-insoluble base material, is preferable. A state, in which 70 wt % or more, especially 80 wt % or more, based on the drug is adhered to the water-absorbing and water-insoluble base material, is especially preferable. In these states, the remaining less than 30 wt % or less than 20 wt % based on the drug is homogeneously dispersed in the composition freely and/or adhered to the water-absorbing and gel-forming base material.

The adhering of a drug to a base material in the present invention indicates a state in which the drug totally exits on the surface of the base material in an adhered state, a part of the drug exits in the base material and the other part exists on the surface of the base material, or the drug totally exists in the base material.

A composition of the present invention, in which a main drug is dispersed in a specifically uneven state, can be manufactured by the following manufacturing method 1, 2 or 3.

The method 1: A drug is mechanically mixed with a water-absorbing and water-insoluble base material, in which at least 90 wt % based on the particles have an average particle diameter in the range of 10-350 μm. Subsequently, a water-absorbing and gel-forming base material, in which at least 90 wt % based on the particles have an average particle diameter in the range of 10-350 μm, is added to the resultant mixture, and they are mechanically mixed.

The method 2: A drug is allowed to adhere to a water-absorbing and water-insoluble base material by freeze drying to obtain a drug-adhered base material. For the freeze drying, the drug and the water-absorbing and water-insoluble base material is dissolved or dispersed in an aqueous solution and the resultant solution or dispersion may be subjected to a freeze drying process. Subsequently, the freeze dried base material is pulverized and sieved so that at least 90 wt % based on the resultant particles have an average particle diameter in the range of 10-350 μm. To the obtained powder fraction, powder of a water-absorbing and gel-forming base material, in which at least 90 wt % based on the particles have an average particle diameter in the range of 10-350 μm, is added, and they are mechanically mixed.

The method 3: A water-absorbing and water-insoluble base material, in which at least 90 wt % based on the particles have an average particle diameter in the range of 10-350 μm, a water-absorbing and gel-forming base material, in which at least 90 wt % based on the particles have an average particle diameter in the range of 10-350 μm and a drug are mechanically mixed by one step.

Among these manufacturing methods, the first and the second manufacturing methods are desirable in that they can easily obtain a composition having a state in which the drug is dispersed more on/in the water-absorbing and water-insoluble base material than on/in the water-absorbing and gel-forming base material. For instance, in the first manufacturing method, the drug can be mixed strongly with the water-absorbing and water-insoluble base material, and subsequently the obtained powdery body can be mixed weakly with the water-absorbing and gel-forming base material. In the second manufacturing method, the mechanical mixing of the obtained powdery body with the water-absorbing and gel-forming base material can be performed either strongly or weakly.

In the first manufacturing method, 60 wt % or more based on the drug in the obtained composition is dispersed in a state adhered to the water-absorbing and water-insoluble base material. In the second manufacturing method, 80 wt % or more based on the drug is dispersed in a state adhered to the water-absorbing and water-insoluble base material. The water-absorbing and gel-forming base material is homogeneously dispersed in the whole compositions.

The third manufacturing method is desirable in that it can easily produce a composition in which the drug is homogeneously dispersed on/in both the water-absorbing and water-insoluble base material and the water-absorbing and gel-forming base material according to the compounding ratio. In this method, the drug and both the base materials can be mixed strongly by one step. For example, 80 wt % or more based on the drug is dispersed according to the compounding ratio of both the base materials. Herein, when the amount of the water-absorbing and water-insoluble base material is 60 wt % based on the total of both the base materials, 48 wt % or more based on the drug is dispersed in a state adhered to the water-absorbing and water-insoluble base material, and the drug which is not adhered to either of the base materials is homogeneously dispersed. In this case, the effect of the present invention is sometimes more or less lowered since the amount of the drug adhered to the water-absorbing and gel-forming base material is somewhat larger than in cases where the drug is dispersed more on/in the water-absorbing and water-insoluble base material.

As another method for manufacturing a composition of the present invention in which a drug is unevenly dispersed more on/in a water-absorbing and water-insoluble base material, the following method can be applied. That is, when a drug is lipophilic, the drug and the water-absorbing and water-insoluble base material are dissolved or dispersed in an organic solvent such as ethanol, and subsequently the resultant solution or dispersion is evaporated. The obtained powder is graded to have an average particle diameter of 10-350 μm, and a water-absorbing and gel-forming base material is added to the resultant powder, and they are mechanically mixed strongly or weakly.

For performing the third manufacturing method, the drug, the water-absorbing and water-insoluble base material and the water-absorbing and gel-forming base material may be dissolved or dispersed in an aqueous solution, the resultant solution or dispersion is freeze dried, and the freeze-dried body is pulverized. By using the obtained powder, one can produce an objective composition.

Further, in the first and the third manufacturing methods, it is preferable to adjust the particle diameters also of the drug to 10-350 μm in at least 90 wt % based on the particles in advance.

In the present invention, the state of uneven existence of a drug can be identified by following processes.

That is, the drug, the water-absorbing and water-insoluble base material and the water-absorbing and gel-forming base material are differently colored with pigments of food additive or fluorescent substances such as fluorescein, respectively.

For instance, when the drug is white powder, the water-absorbing and water-insoluble base material is colored with a pigment such as Blue No. 1, while the water-absorbing and gel forming base material is colored with a different pigment from the pigment used for coloring the water-absorbing and water-insoluble base material. That is, when the water-absorbing and water-insoluble base material is colored with Blue No. 1, the water-absorbing and gel-forming base material is colored with Red No. 3 or Yellow No. 4, and these colorings enable the differentiation of the main drug and the base materials by visual observation, from each other. For the coloring, following methods may be applied. The water-absorbing and water-insoluble base material is immersed in an aqueous solution of a pigment, the mixture is stirred and allowed to stand, and then the resultant mixture is filtered or the solvent of the mixture is evaporated to dry up to obtain the colored base material. For the water-absorbing and gel-forming base material, a pigment is dissolved in an organic solvent such as ethanol, the base material is added to the resultant solution, and the solvent is evaporated to dry up to obtain the colored base material. The obtained film-shaped base material is pulverized into adequate particle sizes.

Concretely, the water-absorbing and water-insoluble base material is colored with Blue No. 1, and the water-absorbing and gel-forming base material is colored with Red No. 3. By using a white powdery main drug and the colored base materials, a composition of the present invention is prepared according to a manufacturing method described above. A small amount of the obtained composition is placed on a slide glass, and the specimen is observed under a microscope having a lens of magnification of 100-1000 times, e.g. 500 times. Thus, it is identified that almost entire part of the white main drug is adhered to the blue-colored water-absorbing and water-insoluble base material, and scarcely adhered to the red-colored water-absorbing and gel-forming base material, i.e. the main drug is unevenly adhered more to the water-absorbing and water-insoluble base material.

Further, by the freeze drying in the second and the third manufacturing methods, one can obtain a composition in which a drug is included in base material(s).

When a composition of the present invention is manufactured by a method other than freeze drying of a drug and base materials, it is preferable to treat the drug in advance so that at least 90 wt % based on the particles have particle diameters in the range of 10-350 μm.

Herein, mechanical mixing in the manufacturing of a composition of the present invention can be performed e.g. by a container rotary-type mixer such as a twin shell blender, a cross-rotary mixer or a double corn mixer, a container fixed-type mixer such as a universal mixer, a ribbon mixer, an automatic mortar or a ball mill, or another type mixer such as a high-speed mixer or a powerful automatic mixer. The mechanical mixing in the present invention also includes manual compression mixing using a mortar.

In the above mixing, strong mixing expresses manual mixing using a mortar, mechanical mixing using a container fixed-type mixer such as a universal mixer, a ribbon mixer, an automatic mortar or a ball mill, or mechanical mixing using a high-speed mixer, a powerful automatic mixer, etc. By these types of mixing, the drug mainly adheres to base materials and is homogeneously mixed in the adhered state. On the other hand, weak mixing expresses mixing using a container rotary-type mixer such as a twin shell blender, a cross-rotary mixer, a double corn mixer or a ball-free ball mill, and the main part of the drug is homogeneously dispersed and mixed without being adhered to base materials in weak mixing.

Further, besides the above-mentioned first to third manufacturing methods, a powdery composition for nasal administration of the present invention can be prepared by specifying particle diameters of base materials. For instance, it can be prepared by (i) adjusting particle diameters of at least 90 wt % based on the particles of a water-absorbing and water-insoluble base material to 10-350 μm, (ii) adjusting particle diameters of at least 90 wt % based on particles of a water-absorbing and gel-forming base material to 10-105 μm, and (iii) making the average particle diameter of the water-absorbing and water-insoluble base material larger than the average particle diameter of the water-absorbing and gel-forming base material.

Especially, a state, in which the average particle diameter of at least 90 wt % based on the particles of a water-absorbing and water-insoluble base material is 10-250 μm and the average particle diameter of at least 90 wt % based on the particles of a water-absorbing and gel-forming base material is 10-105 μm, is preferable since a composition of the state enables increasing in maximum blood concentration. A state, in which the average particle diameter of at least 90 wt % based on the particles of a water-absorbing and water-insoluble base material is 10-250 μm, and the average particle diameter of at least 90 wt % based on the particles of a water-absorbing and gel forming base material is 10-65 μm, is especially preferable since a composition of the state enables further increasing in maximum blood concentration. In both cases, the average particle diameters of the water-absorbing and water-insoluble base material are larger than the average particle diameter of the water-absorbing and gel-forming base material.

Herein, a state, in which the average particle diameter of at least 90 wt % based on the particles of a base material is 10-250 μm, can be identified by classifying particles using testing sieves and giving vibration by hands or machine. That is, at least 90 wt % based on the particles pass through a sieve having an aperture of 250 μm and remain on a sieve having an aperture of 10 μm. While the sieves are being vibrated, the weight of powder on each sieve is measured at appropriate interval, and when the variation of the weight becomes 0.1% or less, the classification of the particles will be completed.

Further, a state, in which the average particle diameter of the water-absorbing and water-insoluble base material is larger than the average particle diameter of the water-absorbing and gel-forming base material, is a state in which the average particle diameters of both the base materials are in the above-mentioned ranges, and at the same time the average particle diameter of the water-absorbing and water-insoluble base material is larger than the average particle diameter of the water-absorbing and gel-forming base material.

A powdery composition for nasal administration of the present invention, in which the average particle diameter of a water-absorbing and water-insoluble base material is larger than that of a water-absorbing and gel-forming base material, can be prepared by a manufacturing method for a powdery preparation common in the art, e.g. the main drug, the water-absorbing and water-insoluble base material and the water-absorbing and gel-forming base material are mechanically mixed.

However, the production of powdery compositions of the present invention by the above-mentioned first to third manufacturing methods is preferable since powdery compositions produced by them can achieve extremely high effects.

As a water-absorbing and water-insoluble base material and a water-absorbing and gel-forming base material of the present invention, as far as it does not contradict the object of the present invention, one can use microspheres having above-mentioned specific properties and comprising a specific kind of base material, e.g. starch or crystalline cellulose, which is known as a base material useful for a powdery composition for nasal administration. Herein, it is preferable to use microspheres having particle diameters in the range of above-mentioned sizes.

The amount of a drug to be used in the present invention, an effective therapeutic dose, depends on the kind of each drug, the kind and severity of disease, the age and body weight of a patient, etc. Generally, it ranges from equal amount to 20 times the amount of the drug to be used for injection, more preferably from equal to 10 times.

Further, the ratio of the amount of a drug to that of base materials (the total of a water-absorbing and water-insoluble base material and a water-absorbing and gel-forming base material) can not be defined indiscriminately since the amount applicable to the nasal cavity is limited and the amount of the drug depends on the therapeutic dose. However, the amount of the base material is preferably 1 pt. wt. or more, especially preferably 5 pts. wt. or more and further especially preferably 10 pts. wt. or more, each based on 1 pt. wt. of the drug.

In order to improve the properties, appearance, or odor of a composition of the present invention, it may optionally contain a lubricant, a binder, a diluent, a coloring agent, a preservative, an antiseptic, a corrigent, etc., known per se. Examples of these additives are cited as follows: talc, stearic acid, its salt, a wax, etc., as the lubricant; a starch, a dextrin, etc., as the binder; a starch, lactose, etc., as the diluent; Red No. 2, etc., as the coloring agent; ascorbic acid, etc., as the preservative; a p-hydroxybenzoate ester, etc., as the antiseptic; and menthol, etc., as the corrigent.

In order to administer a composition of the present invention, it is formulated into an adequate administration form. As the administration form, there is a capsule in which each administration dose of the composition is placed. The composition in the capsule is sprayed into the nasal cavities by an adequate administration device. Also, a composition of the present invention in an amount of one dose or plural doses is placed in an adequate container, and the composition in an amount of one dose may be administered by single dosage or divided dosage.

INDUSTRIAL FIELD OF APPLICATION

Thus, the present invention provides a powdery composition for nasal administration excellent in absorption from the nasal cavity and capable of exhibiting extreme increase in maximum blood concentration compared with a conventional composition for nasal administration even for a drug having a high solubility in water, a drug having a high lipophilicity or a peptide/proteinaceous drug having a large molecular weight.

Not only for an expensive peptide/proteinaceous drug but also for a non-peptide/non-proteinaceous drug, a powdery composition for nasal administration of the present invention gives an extremely high maximum blood concentration even with same dose as in a conventional composition, and accordingly the use of the drug can be reduced. The composition also can reduce fluctuation of blood concentration and stably obtain the objective pharmaceutical effect.

Further, a powdery composition for nasal administration of the present invention is excellent in the absorption and durability of blood concentration similarly to a conventional powdery composition for nasal administration. However, differently from the conventional composition, the composition of the present invention needs no absorption stimulator having irritation, and it is safe and expected to stably achieve the desired therapeutic effect.

Therefore, the present invention has an extremely deep meaning for medicinal therapy which is carried out by administering a non-injection type drug.

EXAMPLES

The following Examples and Comparative Examples illustrate the present invention more specifically. However, it should not be understood that these examples are given to limit the scope of the invention.

In the following examples, etc., crystalline cellulose is sometimes expressed by microcrystalline cellulose and abbreviated as CC, and hydroxypropyl cellulose is abbreviated as HPC.

Examples 1 to 4 and Comparative Examples 1 to 5

To 10 mg of beclometasone dipropionate (produced by SICOR Co.), one of anti-inflammatory steroids, 150 mg of base material component (CC+HPC) having a composition shown in Table 1 was added in a mortal and mixed, and then 0.16 mg of magnesium stearate as a lubricant was added to the mixture to prepare a powdery composition (Examples 1 to 4 and Comparative Examples 1 to 5).

Microcrystalline cellulose (Avicel PH101 produced by Asahi Kasei Co.) used here had an average particle diameter of 100-250 μm in at least 90 wt % based on the particles. Hydroxypropyl cellulose (HPC-H produced by Nippon Soda Co.) used here had an average particle diameter of 10-100 μm in at least 90 wt % based on the particles.

Each of the compositions prepared above was administered into the nasal cavity of a male Japanese white rabbit (weighing 2.5-3.0 kg) with a powder sprayer (Puvlizer® made by Teijin Co.) so that the dose of the composition became 2 mg/kg. The blood samples were withdrawn from the ear vein periodically after the administration, and beclometasone dipropionate levels in blood were determined by RIA and the results are shown in Table 1.

When the ratio of hydroxypropyl cellulose to the total of the base materials was in the range of 5-40 wt %, the composition exhibited a higher maximum blood concentration than the composition in which hydroxypropyl cellulose was absent (Comparative Example 1), and when the ratio was in the range of 30-40 wt %, the composition (Example 3 or 4) exhibited especially higher blood concentrations. These results show that the compositions of the present invention exhibited extreme improvement of absorption and large increases in maximum blood concentrations.

TABLE 1

Time Course of Beclometasone Dipropionate Level in Blood after Administration of Each Composition

|  | CC* | HPC* | 15 min | 30 min | 45 min | 60 min | 90 min (pg/ml) |
|---|---|---|---|---|---|---|---|
| Example 1 | 95 | 5 | 100 | 140 | 120 | 90 | 40 |
| Example 2 | 80 | 20 | 100 | 160 | 140 | 100 | 50 |
| Example 3 | 70 | 30 | 105 | 160 | 180 | 120 | 60 |
| Example 4 | 60 | 40 | 105 | 160 | 200 | 140 | 80 |
| Comp. Ex. 1 | 100 | 0 | 95 | 130 | 100 | 60 | 20 |
| Comp. Ex. 2 | 50 | 50 | 80 | 100 | 120 | 80 | 40 |
| Comp. Ex. 3 | 40 | 60 | 70 | 90 | 90 | 70 | 40 |
| Comp. Ex. 4 | 20 | 80 | 35 | 40 | 30 | 15 | 10 |
| Comp. Ex. 5 | 0 | 100 | 20 | 25 | 25 | 20 | 15 |

*Numbers in the columns of CC and HPC express weight ratios. (As far as it is not specified, the same is applied in the following tables)

In the compositions obtained in Examples 1 to 4, the drug was unevenly dispersed on CC according to the ratio of the base materials.

Examples 5 to 8 and Comparative Examples 6-10

To 100 mg of metoclopramide (produced by SIGMA Co.), one of antiemetic drugs, 200 mg of each of the various base material components (CC+HPC) shown in Table 2 was added in a ball mill and mixed, and then 0.30 mg of magnesium stearate as a lubricant was added to the mixture to prepare a powdery composition (Examples 5 to 8 and Comparative Examples 6 to 10). Microcrystalline cellulose (Avicel PH101 produced by Asahi Kasei Co.) used here had an average particle diameter of 50-350 μm in at least 90 wt % based on the particles. Hydroxypropyl cellulose (HPC-H produced by Nippon Soda Co.) used here had an average particle diameter of 10-100 μm in at least 90 wt % based on the particles.

Each of the compositions prepared above was administered into the nasal cavity of a male Japanese white rabbit (weighing 2.5-3.0 kg) with a powder sprayer (Puvlizer® made by Teijin Co.) so that the dose of the composition became 3 mg/kg. The blood samples were withdrawn from the ear vein periodically after the administration, and metoclopramide levels in blood (ng/ml) were determined by HPLC and the results are shown in Table 2. When the ratio of hydroxypropyl cellulose to the total of the base materials was in the range of 5-40 wt %, a composition of the present invention exhibited a higher maximum blood concentration than the composition in which hydroxypropyl cellulose was absent (Comparative Example 6), and when the ratio was in the range of 30-40 wt %, a composition (Example 7 or 8) exhibited especially higher blood concentrations. These results show that the compositions of the present invention exhibited extreme improvement of absorption and large increases in maximum blood concentrations.

TABLE 2

Time Course of Metoclopramide Level in Blood after Administration of Each Composition

|  | CC | HPC | 30 min | 60 min | 90 min | 120 min | 240 min (ng/ml) |
|---|---|---|---|---|---|---|---|
| Example 5 | 95 | 5 | 15 | 35 | 40 | 30 | 20 |
| Example 6 | 80 | 20 | 20 | 40 | 50 | 35 | 25 |
| Example 7 | 70 | 30 | 30 | 60 | 80 | 70 | 50 |
| Example 8 | 60 | 40 | 30 | 60 | 75 | 60 | 45 |
| Comp. Ex. 6 | 100 | 0 | 15 | 30 | 35 | 20 | 10 |
| Comp. Ex. 7 | 50 | 50 | 10 | 20 | 20 | 15 | 5 |
| Comp. Ex. 8 | 40 | 60 | 10 | 15 | 15 | 15 | 5 |
| Comp. Ex. 9 | 20 | 80 | 5 | 10 | 15 | 10 | 10 |
| Comp. Ex. 10 | 0 | 100 | 5 | 5 | 10 | 5 | 0 |

In the compositions of Examples 5 to 8, the drug was unevenly dispersed on CC according to the ratio of the base materials.

Examples 9 to 11 and Comparative Examples 11 to 15

To 10 mg of leuprolide acetate (produced by Bachem Co.), one of luteinizing hormones, 200 mg of each of the various base material components (CC+HPC) shown in Table 3 was added and mixed, and then 0.21 mg of magnesium stearate as a lubricant was added to the mixture to prepare a powdery composition (Examples 9 to 11 and Comparative Examples 11 to 15). The leuprolide acetate was prepared by pulverizing a freeze dried product in a mortar so that the particles had particle diameters of 10-150 μm in at least 90 wt % based on the particles. Microcrystalline cellulose (Avicel PH101 produced by Asahi Kasei Co.) used here had an average particle diameter of 50-350 μm in at least 90 wt % based on the particles. Hydroxypropyl cellulose (HPC-H produced by Nippon Soda Co.) used here had an average particle diameter of 10-100 μm in at least 90 wt % based on the particles.

Each of the compositions prepared above was administered into the nasal cavity of a male Japanese white rabbit (weighing 2.5-3.0 kg) with a powder sprayer (Puvlizer® made by Teijin Co.) so that the dose of the composition became 2.5 mg/kg. The blood samples were withdrawn from the ear vein periodically after the administration, and leuprolide acetate levels (ng/ml) in blood were determined by RIA. At the same time, as Reference Example 1, an aqueous solution of leuprolide acetate was administered. The results are shown in Table 3.

When a ratio of hydroxypropyl cellulose to the total of the base materials was in the range of 5-30 wt %, a composition of the present invention exhibited a higher maximum blood concentration than the composition in which hydroxypropyl cellulose was absent (Comparative Example 11), and when the ratio was in the range of 20-30 wt %, a composition (Example 10 or 11) exhibited especially higher blood concentrations. These results show that the compositions of the present invention exhibited extreme improvement of absorption and large increases in maximum blood concentrations.

TABLE 3

Time Course of Leuprolide Acetate Level in Blood after Administration of Each Composition

| | CC | HPC | 15 min | 30 min | 45 min | 60 min | 90 min | 120 min | 180 min (ng/ml) |
|---|---|---|---|---|---|---|---|---|---|
| Example 9 | 95 | 5 | 70 | 100 | 110 | 95 | 70 | 60 | 45 |
| Example 10 | 80 | 20 | 80 | 130 | 140 | 120 | 85 | 70 | 60 |
| Example 11 | 70 | 30 | 85 | 135 | 145 | 130 | 105 | 95 | 80 |
| Comp. Ex. 11 | 100 | 0 | 35 | 40 | 50 | 40 | 40 | 20 | 10 |
| Comp. Ex. 12 | 60 | 40 | 40 | 50 | 50 | 45 | 40 | 30 | 25 |
| Comp. Ex. 13 | 50 | 50 | 40 | 45 | 50 | 50 | 45 | 40 | 30 |
| Comp. Ex. 14 | 25 | 75 | 35 | 45 | 45 | 50 | 45 | 40 | 30 |
| Comp. Ex. 15 | 0 | 100 | 15 | 20 | 20 | 20 | 20 | 15 | 10 |
| Ref. Ex. 1 | — | — | 0 | 5 | 10 | 5 | 0 | 0 | 0 |

Further, the drug and each of microcrystalline cellulose components (CC) in the amounts corresponding to the compositions of the above Examples 9 to 11 were added to 100 ml of purified water and dispersed or dissolved, and the resultant dispersion or solution was freeze dried. The obtained solid was pulverized in a mortal, and the resultant particles were classified so that at least 90 wt % based on the particles had an average particle diameter of 50-350 µm. Subsequently, hydroxypropyl cellulose was added to the classified portion of particles, the mixture was mixed by a high-speed mixer, and a lubricant was added to prepare a powdery composition.

In the obtained compositions of Examples 9 to 11, the drug existed in a state in which it was unevenly dispersed more on the water-absorbing and water-insoluble base material.

Each of the powdery compositions of Examples 9 to 11 gave an extremely high maximum blood concentration of 100 ng/ml or more at 45 min after administration.

Examples 12 to 14 and Comparative Examples 16 to 21

To 0.10 mg of salmon calcitonin (produced by Bachem Co.), one of calcitonins, 150 mg of each of the various base material components (CC+HPC) shown in Table 4 was added in a mortal and mixed, and then 0.16 mg of magnesium stearate as a lubricant was added to the mixture to prepare a powdery composition (Examples 12 to 14 and Comparative Examples 16 to 21). The salmon calcitonin was prepared by pulverizing a freeze dried product in a mortar so that the particles had particle diameters of 10-150 µm in at least 90 wt % based on the particles. Microcrystalline cellulose (Avicel PH101 produced by Asahi Kasei Co.) used here had an average particle diameter of 50-350 µm in at least 90 wt % based on the particles. Hydroxypropyl cellulose (HPC-H produced by Nippon Soda Co.) used here had an average particle diameter of 10-100 µm in at least 90 wt % based on the particles.

Each of the compositions prepared above was administered into the nasal cavity of a male Japanese white rabbit (weighing 2.5-3.0 kg) with a powder sprayer (Puvlizer® made by Teijin Co.) so that the dose of the composition became 0.6 mg/kg. The blood samples were withdrawn from the ear vein periodically after the administration, and salmon calcitonin levels (pg/ml) in blood were determined by RIA. At the same time, as Reference Example 2, an aqueous solution of salmon calcitonin was administered. The results are shown in Table 4.

When a ratio of hydroxypropyl cellulose to the total of the base materials was in the range of 5-20 wt %, a composition of the present invention exhibited a higher maximum blood concentration than the composition in which hydroxypropyl cellulose was absent (Comparative Example 16), and when the ratio was in the range of 10-20 wt %, a composition (Example 13 or 14) exhibited especially higher blood concentrations. These results show that compositions of the present invention exhibited extreme improvement of absorption and large increases in maximum blood concentrations.

TABLE 4

Time Course of Salmon Calcitonin Level in Blood after Administration of Each Composition

| | CC | HPC | 15 min | 30 min | 45 min | 60 min | 90 min | 120 min | 180 min (pg/ml) |
|---|---|---|---|---|---|---|---|---|---|
| Example 12 | 95 | 5 | 25 | 50 | 45 | 35 | 25 | 15 | 5 |
| Example 13 | 90 | 10 | 30 | 80 | 70 | 50 | 40 | 20 | 10 |
| Example 14 | 80 | 20 | 30 | 70 | 75 | 65 | 55 | 35 | 20 |
| Comp. Ex. 16 | 100 | 0 | 5 | 25 | 40 | 20 | 10 | 0 | 0 |
| Comp. Ex. 17 | 70 | 30 | 5 | 20 | 15 | 15 | 5 | 5 | 0 |
| Comp. Ex. 18 | 60 | 40 | 5 | 15 | 15 | 15 | 10 | 5 | 5 |
| Comp. Ex. 19 | 50 | 50 | 0 | 5 | 10 | 10 | 5 | 5 | 5 |
| Comp. Ex. 20 | 25 | 75 | 0 | 5 | 5 | 5 | 0 | 0 | 0 |
| Comp. Ex. 21 | 0 | 100 | 0 | 5 | 5 | 5 | 0 | 0 | 0 |
| Ref. Ex. 2 | — | — | 0 | 5 | 5 | 0 | 0 | 0 | 0 |

Further, the drug and each of microcrystalline cellulose components (CC) in the amounts corresponding to the compositions of the above Examples 12 to 14 were added to 100 ml of purified water and dispersed or dissolved, and the resultant dispersion or solution was freeze dried. The obtained solid was pulverized in a mortar, and the particles were classified so that at least 90 wt % based on the particles had an average particle diameter of 50-350 μm. Subsequently, hydroxypropyl cellulose was added to the classified portion of particles, the mixture was mixed by a twin shell blender, and a lubricant was added to prepare a powdery composition.

In the obtained compositions of Examples 12 to 14, the drug existed in a state in which it was unevenly dispersed on the water-absorbing and water-insoluble base material in at least 90 wt % based on the drug.

Teijin Co.) so that the dose of the composition became 2.5 mg/kg. The blood samples were withdrawn from the ear vein periodically after the administration, and human growth hormone levels in blood were determined by RIA. Further, at the same time, an aqueous solution of human growth hormone was administered as Reference Example 3. The results are shown in Table 5. When a ratio of hydroxypropyl cellulose to the total of the base materials was in the range of 5-20 wt %, a composition of the present invention exhibited a higher maximum blood concentration than the composition in which hydroxypropyl cellulose was absent (Comparative Example 24), and when the ratio was in the range of 10-20 wt %, a composition (Example 16 or 17) exhibited especially higher blood concentrations. It is clear from these results that the compositions of the Examples exhibited extreme improvement of absorption and large increases in maximum blood concentrations.

TABLE 5

Time Course of Human Growth Hormone Level in Blood after Administration of Each Composition

| | CC | HPC | 15 min | 30 min | 45 min | 60 min | 90 min | 120 min | (ng/ml) 180 min |
|---|---|---|---|---|---|---|---|---|---|
| Example 15 | 95 | 5 | 15 | 35 | 25 | 20 | 15 | 10 | 5 |
| Example 16 | 90 | 10 | 25 | 70 | 55 | 35 | 25 | 10 | 5 |
| Example 17 | 80 | 20 | 25 | 60 | 75 | 55 | 35 | 25 | 15 |
| Comp. Ex. 22 | 100 | 0 | 10 | 20 | 15 | 10 | 5 | 0 | 0 |
| Comp. Ex. 23 | 70 | 30 | 5 | 15 | 15 | 10 | 5 | 5 | 0 |
| Comp. Ex. 24 | 60 | 40 | 5 | 10 | 15 | 15 | 10 | 5 | 5 |
| Comp. Ex. 25 | 50 | 50 | 0 | 5 | 10 | 10 | 5 | 5 | 0 |
| Comp. Ex. 26 | 25 | 75 | 0 | 5 | 5 | 10 | 5 | 0 | 0 |
| Comp. Ex. 27 | 0 | 100 | 0 | 5 | 5 | 0 | 0 | 0 | 0 |
| Ref. Ex. 3 | — | — | 0 | 5 | 0 | 0 | 0 | 0 | 0 |

Each of the powdery compositions of Examples 12 to 14 gave an extremely high maximum blood concentration of 50 pg/ml or more at 30-45 min after administration.

Examples 15 to 17 and Comparative Examples 22 to 27

To 10 mg of human growth hormone (produced by Bachem Co.), one of growth hormones, 240 mg of each of the various base material components (CC+HPC) shown in Table 5 was added in a mortal and mixed, and then 0.25 mg of magnesium stearate as a lubricant was added to the mixture to prepare a powdery composition (Examples 15 to 17 and Comparative Examples 22 to 27). The human growth hormone was prepared by pulverizing a freeze dried product in a mortal so that the particles had an average particle diameter of 10-150 μm in at least 90 wt % based on the particles. Microcrystalline cellulose (Avicel PH101 produced by Asahi Kasei Co.) used here had an average particle diameter of 50-350 μm in at least 90 wt % based on the particles. Hydroxypropyl cellulose (HPC-H produced by Nippon Soda Co.) used here had an average particle diameter of 10-100 μm in at least 90 wt % based on the particles.

Each of the compositions prepared above was administered into the nasal cavity of a male Japanese white rabbit (weighing 2.5-3.0 kg) with a powder sprayer (Puvlizer® made by Examples 18 to 26 and Comparative Examples 28 to 36

Compositions (Examples 18 to 26), each of which contained leuprolide acetate (produced by Bachem Co.) as a main drug and had a weight ratio between two base materials, i.e. the ratio of a water-absorbing and water-insoluble base material to a water-absorbing and gel-forming base material of 80:20, were prepared by using the two kinds of base materials shown in Table 6. The compositions were administered to rabbits under the same conditions as in Examples 9 to 11. Further, compositions of Comparative Examples 28 to 36 were prepared by using the base materials shown in the table, and they were administered to rabbits. The water-absorbing and water-insoluble base materials used here had an average particle diameter of 50-350 μm in at least 90 wt % based on the particles, and the water-absorbing and gel-forming base material used here had an average particle diameter of 10-100 μm in at least 90 wt % based on the particles.

The obtained maximum blood concentrations and times of their samplings are shown in Table 6. It is clear that Examples 18 to 26 gave extremely high maximum blood concentrations while Comparative Examples 28 to 36 were good in absorption but low in maximum blood concentrations comparing the compositions of the present invention.

TABLE 6

Maximum Blood Concentration of Leuprolide Acetate and Time after Administration of Each Composition

| | Water-absorbing & water-insoluble base material | Water-absorbing & gel-forming base material | Maximum blood conc. (pg/ml) | Time of maximum blood conc. (min) |
|---|---|---|---|---|
| Example 18 | α-cellulose | HPC | 120 | 45 |
| Example 19 | cross-linked CMCNa | " | 125 | 45 |
| Example 20 | cross-linked starch | " | 100 | 30 |
| Example 21 | gelatin | " | 120 | 45 |
| Example 22 | casein | " | 110 | 40 |
| Example 23 | tragacanth gum | " | 105 | 30 |
| Example 24 | polyvinyl pyrrolidone | " | 90 | 30 |
| Example 25 | chitin | " | 115 | 45 |
| Example 26 | chitosan | " | 125 | 45 |
| Comp. Ex. 28 | hydroxy-propyl starch | " | 65 | 30 |
| Comp. Ex. 29 | carboxy-methyl starch | " | 50 | 30 |
| Comp. Ex. 30 | amylose | " | 60 | 30 |
| Comp. Ex. 31 | amylopectin | " | 55 | 30 |
| Comp. Ex. 32 | pectin | " | 75 | 30 |
| Comp. Ex. 33 | sodium casein | " | 70 | 30 |
| Comp. Ex. 34 | gum arabic | " | 60 | 30 |
| Comp. Ex. 35 | gluco-mannan | " | 55 | 30 |
| Comp. Ex. 36 | cross-linked polyacrylic acid Na | " | 60 | 30 |

Examples 27 to 30 and Comparative Examples 37 to 42

Compositions similar to those of Examples 27 to 30, which contained leuprolide acetate (produced by Bachem Co.) as a main drug and each of which had a weight ratio between two base materials, i.e. the ratio of a water-absorbing and water-insoluble base material to a water-absorbing and gel-forming base material of 80:20, were prepared by using the two kinds of base materials shown in Table 7. The compositions were administered to rabbits under same conditions as in Examples 9 to 11. Further, compositions of Comparative Examples 37 to 42 were prepared by using the base materials shown in the table in the same manner as in Examples 27 to 30, and they were administered to rabbits. The water-absorbing and water-insoluble base materials shown in Table 7 had an average particle diameter of 50-350 μm in at least 90 wt % based on the particles, and the water-absorbing and gel-forming base material had an average particle diameter of 10-100 μm in at least 90 wt % based on the particles.

The obtained maximum blood concentrations and times of their samplings are shown in Table 7. It is clear that Examples 27 to 30 gave extremely high maximum blood concentrations while Comparative Examples 37 to 42 were good in absorption, but they had lower maximum blood concentrations than the compositions of the present invention.

TABLE 7

Maximum Blood Concentration of Leuprolide Acetate and Time after Administration of Each Composition

| | Water-absorbing & water-insoluble base material | Water-absorbing & gel-forming base material | Maximum blood conc. (pg/ml) | Time of maximum blood conc. (min) |
|---|---|---|---|---|
| Example 27 | microcrystalline cellulose | hydroxy-propylmethyl cellulose | 120 | 45 |
| Example 28 | microcrystalline cellulose | methyl cellulose | 115 | 45 |
| Example 29 | microcrystalline cellulose | hydroxy-ethyl cellulose | 95 | 30 |
| Example 30 | microcrystalline cellulose | Na carboxy-methyl cellulose | 125 | 45 |
| Comp. Ex. 37 | microcrystalline cellulose | Na polyacrylate | 70 | 30 |

TABLE 7-continued

Maximum Blood Concentration of Leuprolide Acetate and Time after Administration of Each Composition

| | Water-absorbing & water-insoluble base material | Water-absorbing & gel-forming base material | Maximum blood conc. (pg/ml) | Time of maximum blood conc. (min) |
|---|---|---|---|---|
| Comp. Ex. 38 | microcrystalline cellulose | K polyacrylate | 65 | 30 |
| Comp. Ex. 39 | microcrystalline cellulose | polyethylene glycol | 50 | 30 |
| Comp. Ex. 40 | microcrystalline cellulose | polyvinyl pyrrolidone | 55 | 30 |
| Comp. Ex. 41 | microcrystalline cellulose | amylose | 55 | 30 |
| Comp. Ex. 42 | microcrystalline cellulose | pullulan | 60 | 30 |

Examples 31 to 57

For each drug shown in Table 8, a powdery composition was prepared using base materials in which a ratio of hydroxypropyl cellulose to the total of hydroxypropyl cellulose and microcrystalline cellulose was 5, 10, 20, 30, 40 or 50 wt %, and the composition was administered to a rabbit. Blood concentrations of the drug were determined by using radioactivity, in a same manner as described in above examples. Also, for each drug shown in the table, a powdery composition was prepared using only microcrystalline cellulose as base material, and the composition was administered to a rabbit. The microcrystalline cellulose used here had an average particle diameter of 50-350 μm in at least 90 wt % based on the particles, and the hydroxypropyl cellulose used here had an average particle diameter of 10-100 μm in at least 90 wt % based on the particles.

Relative values of the maximum blood concentrations of the compositions prepared using the base material components comprising hydroxypropyl cellulose and microcrystalline cellulose to the maximum blood concentration (=1.0) of the composition prepared using the base material component comprising only microcrystalline cellulose are shown in Table 8. It is clear from these results that in the case of a non-peptide/non-proteinaceous drug, when the hydroxypropyl cellulose ratio to the total of the base materials was 5-40 wt %, the composition gave extreme increase in the maximum blood concentration, and when the ratio was 30-40 wt %, it gave especially extreme increase in the maximum blood concentration. In the case of a peptide/protein-aceous drug having a molecular weight of not less than 500 and less than 1500, when the hydroxypropyl cellulose ratio was 5-30 wt %, the composition gave extreme increase in the maximum blood concentration, and when the ratio was 20-30 wt %, it gave especially extreme increase in the maximum blood concentration. In the case of a peptide/proteinaceous drug having a molecular weight of not less than 1500 nor more than 30,000, when the hydroxypropyl cellulose ratio was 5-20 wt %, the composition gave extreme increase in the maximum blood concentration, and when the ratio was 10-20 wt %, it gave especially extreme increase in the maximum blood concentration.

TABLE 8

Relative Value of Maximum Blood Concentration after Administration of Composition Containing Each Drug

| | Kind of Drug | Relative value of maximum blood concentration | | | | | |
|---|---|---|---|---|---|---|---|
| | | 5* | 10 | 20 | 30 | 40 | 50 |
| Example 31 | 4-$^{14}$C-testosterone | 2.3 | 2.5 | 2.7 | 3.5 | 3.1 | 1.8 |
| Example 32 | N-methyl-$^{3}$H-tamoxifen | 2.0 | 2.2 | 2.6 | 3.2 | 3.0 | 1.6 |
| Example 33 | N-methyl-$^{3}$H-scopolamine | 2.2 | 2.6 | 3.0 | 3.2 | 3.1 | 1.4 |
| Example 34 | 4-$^{3}$H-propranolol HCl | 2.0 | 2.4 | 2.6 | 3.6 | 3.0 | 1.5 |
| Example 35 | 1,2,6,7-$^{3}$H-progesterone | 2.0 | 2.4 | 2.8 | 3.8 | 3.2 | 1.8 |
| Example 36 | 6,7-$^{3}$H-estradiol | 2.4 | 2.8 | 3.1 | 4.0 | 3.5 | 1.3 |
| Example 37 | O-methyl-$^{3}$H-melatonin | 2.0 | 2.2 | 2.2 | 2.8 | 3.0 | 1.2 |
| Example 38 | $^{3}$H-imipramine | 2.6 | 2.6 | 2.9 | 3.2 | 2.8 | 0.9 |
| Example 39 | 7,8-$^{3}$H-dopamine | 2.1 | 2.5 | 2.7 | 3.0 | 3.0 | 1.8 |
| Example 40 | 2-$^{14}$C-diazepam | 2.2 | 2.4 | 2.8 | 3.5 | 3.0 | 1.5 |
| Example 41 | 1,2,4-$^{3}$H-dexamethasone | 2.5 | 3.0 | 3.2 | 5.0 | 4.2 | 0.6 |
| Example 42 | N-methyl-$^{3}$H-cimetidine | 2.2 | 2.4 | 2.8 | 3.0 | 3.0 | 1.8 |
| Example 43 | 3,5-$^{3}$H-enkephalin (MW = 556) | 2.0 | 2.1 | 2.2 | 2.5 | 1.4 | 0.4 |
| Example 44 | 3-$^{125}$I-ACTH 3-9 (MW = 1068) | 2.0 | 2.2 | 2.4 | 2.6 | 1.8 | 1.1 |
| Example 45 | 2,8-$^{125}$I-vasopressin (MW = 1208) | 2.2 | 2.6 | 3.0 | 2.5 | 1.6 | 0.8 |
| Example 46 | $^{125}$I-hirudin 55-65 (MW = 1412) | 2.1 | 2.2 | 2.5 | 2.5 | 1.2 | 0.4 |
| Example 47 | $^{125}$I-sandostatin (MW = 900) | 2.4 | 2.4 | 2.8 | 2.6 | 1.3 | 0.4 |
| Example 48 | 2-$^{125}$I-oxytocin (MW = 1131) | 2.2 | 2.2 | 2.6 | 3.0 | 1.8 | 1.0 |
| Example 49 | 8-$^{125}$I-bradykinin (MW = 1200) | 2.0 | 2.1 | 2.8 | 2.8 | 2.2 | 1.2 |
| Example 50 | $^{125}$I-insulin (MW = 6000) | 1.8 | 2.0 | 1.4 | 1.2 | 1.1 | 0.6 |
| Example 51 | $^{125}$I-glucagon (MW = 3606) | 2.6 | 2.8 | 2.1 | 1.4 | 1.2 | 0.2 |
| Example 52 | $^{125}$I-h growth hormone (MW = 21500) | 2.8 | 2.2 | 1.8 | 1.2 | 1.0 | 0.1 |
| Example 53 | $^{125}$I-h growth hormone releasing factor (MW = 5040) | 2.2 | 2.6 | 2.0 | 1.2 | 1.0 | 0.4 |
| Example 54 | $^{125}$I-h atrial natriuretic peptide 4-28 (MW = 2724) | 3.6 | 4.0 | 2.4 | 1.8 | 1.2 | 0.8 |
| Example 55 | 1-$^{125}$I-h parathyroid hormone 1-34 (MW = 4194) | 4.0 | 2.8 | 2.0 | 1.4 | 1.2 | 0.6 |
| Example 56 | $^{125}$I-rh interleukin-2 (MW = 15000) | 3.0 | 2.2 | 2.0 | 1.4 | 1.2 | 0.1 |
| Example 57 | $^{125}$I-rh interferon gamma (MW = 17200) | 2.8 | 2.0 | 1.8 | 1.2 | 1.0 | 0.2 |

*HPC ratio (%)

Examples 58 to 60 and Comparative Examples 43 to 48

To 10 mg of estradiol dipropionate (produced by Wako Junyaku Co.), one of sex hormones, microcrystalline cellulose (Avicel PH101 produced by Asahi Kasei Co.) and Hydroxypropyl cellulose (HPC-H produced by Nippon Soda Co.) in amounts of 140 mg and 60 mg, respectively, whose particle diameters had been adjusted to the sizes shown in Table 9 in advance, were added and mixed, and then 0.21 mg of magnesium stearate as a lubricant was added to the mixture to prepare a powdery composition (Examples 58 to 60 and Comparative Examples 43 to 48).

Each of the compositions prepared above was administered into the nasal cavity of a male Japanese white rabbit (weighing 2.5-3.0 kg) with a powder sprayer (Puvlizer® made by Teijin Co.) so that the dose of the composition became 2 mg/kg. The blood samples were withdrawn from the ear vein periodically after the administration, and estradiol dipropionate levels in blood were determined by RIA. The results are shown in Table 9. When microcrystalline cellulose, the water-absorbing and water-insoluble base material, had particle diameters of 50-350 μm in 90 wt % based on the particles and hydroxypropyl cellulose, the water-absorbing and gel-forming base material, had particle diameters of 10-100 μm in 90 wt % based on the particles, the composition (Example 58) exhibited a higher maximum blood concentration than the compositions of the comparative examples (Comparative Examples 43 to 48). Further, when microcrystalline cellulose, the water-absorbing and water-insoluble base material, had particle diameters of 50-350 μm in 90 wt % based on the particles and hydroxypropyl cellulose, the water-absorbing and gel-forming base material, had particle diameters of 20-50 μm in 90 wt % based on the particles (Example 59) and when microcrystalline cellulose, the water-absorbing and water-insoluble base material, had particle diameters of 100-250 μm in 90 wt % based on the particles and hydroxypropyl cellulose, the water-absorbing and gel-forming base material, had particle diameters of 20-50 μm in 90 wt % based on the particles (Example 60), the compositions of both the examples exhibited further extremely higher maximum blood concentrations. It is clear that the compositions of the Examples exhibited extreme improvement in absorption and large increases in maximum blood concentrations.

cellulose (HPC-H produced by Nippon Soda Co.) in amounts of 120 mg and 30 mg, respectively, whose particle diameters had been adjusted to the sizes shown in Table 10 in advance, were added and mixed. Subsequently, 0.16 mg of magnesium stearate as a lubricant was added to the mixture to prepare a powdery composition (Examples 61 to 63 and Comparative Examples 49 to 54).

Each of the compositions prepared above was administered into the nasal cavity of a male Japanese white rabbit (weighing 2.5-3.0 kg) with a powder sprayer (Puvlizer® made by Teijin Co.) so that the dose of the composition became 0.6 mg/kg. The blood samples were withdrawn from the ear vein periodically after the administration, and salmon calcitonin levels in blood were determined by RIA. The results are shown in Table 10. When microcrystalline cellulose had particle diameters of 50-350 μm in at least 90 wt % based on the particles and hydroxypropyl cellulose had particle diameters of 10-100 μm in at least 90 wt % based on the particles (Example 61), the composition exhibited a higher maximum blood concentration than the compositions of the comparative examples (Comparative Examples 49 to 54). Further, when microcrystalline cellulose had particle diameters of 100-250 μm in at least 90 wt % based on the particles and hydroxypropyl cellulose had particle diameters of 10-100 μm in at least 90 wt % based on the particles (Example 62) and when microcrystalline cellulose had particle diameters of 100-250 μm in at least 90 wt % based on the particles and hydroxypropyl cellulose had particle diameters of 20-50 μm in at least 90 wt % based on the particles (Example 63), the compositions of both the examples exhibited further extremely higher blood concentrations. It is clear that the compositions of the Examples exhibited extreme improvement in absorption and large increases in maximum blood concentrations. On the other hand, when microcrystalline cellulose and hydroxypropyl cellulose had each an average particle diameter of 20-150 μm in at least 90 wt % based on the particles (Comparative Example 49), the composition exhibited somewhat longer durability but did not exhibit any difference regarding maximum blood concentration compared with the composition of the case of microcrystalline cellulose alone (Comparative Example 54). When microcrystalline cellulose had an average particle diameter of 20-50 μm in at least 90 wt % based on the particles and hydroxypropyl cellulose had an average particle diameters of 100-250 μm in at least 90 wt % based on the particles (Comparative Example 51), the maximum blood concentration of the composition were extremely lower than that of the composition of the case of microcrystalline cellulose alone (Comparative Example 54).

TABLE 9

Time Course of Blood Concentration of Estradiol Dipropionate after Administration of Each Composition

|  | CC | HPC | 15 min | 30 min | 45 min | 60 min | 90 min | 120 min | (ng/ml) 180 min |
|---|---|---|---|---|---|---|---|---|---|
| Example 58 | 50-350 | 10-100 | 15 | 55 | 65 | 50 | 35 | 20 | 15 |
| Example 59 | 50-350 | 20-50 | 15 | 65 | 75 | 60 | 45 | 20 | 15 |
| Example 60 | 100-250 | 20-50 | 25 | 60 | 75 | 55 | 40 | 25 | 15 |
| Comp. Ex. 43 | 20-150 | 20-150 | 5 | 25 | 30 | 30 | 25 | 10 | 5 |
| Comp. Ex. 44 | 100-350 | 20-150 | 10 | 20 | 30 | 30 | 25 | 15 | 5 |
| Comp. Ex. 45 | 20-50 | 100-250 | 0 | 10 | 10 | 5 | 5 | 0 | 0 |
| Comp. Ex. 46 | 10-50 | 100-250 | 5 | 15 | 25 | 15 | 10 | 5 | 0 |
| Comp. Ex. 47 | 150-250 | 100-250 | 5 | 15 | 10 | 5 | 5 | 0 | 0 |
| Comp. Ex. 48 | 20-150 | 100-250 | 5 | 25 | 35 | 20 | 15 | 5 | 0 |

Examples 61 to 63 and Comparative Examples 49-54

To 0.10 mg of salmon calcitonin (produced by Bachem Co.), one of calcitonins, microcrystalline cellulose (Avicel PH101 produced by Asahi Kasei Co.) and hydroxypropyl

TABLE 10

Time Course of Blood Concentration of Salmon Calcitonin after Administration of Each Composition

|  | CC | HPC | 15 min | 30 min | 45 min | 60 min | 90 min | 120 min | (pg/ml) 180 min |
|---|---|---|---|---|---|---|---|---|---|
| Example 61 | 50-350 | 10-100 | 30 | 70 | 75 | 65 | 55 | 35 | 20 |
| Example 62 | 100-250 | 10-100 | 30 | 75 | 85 | 75 | 65 | 35 | 20 |
| Example 63 | 100-250 | 20-50 | 25 | 75 | 90 | 85 | 65 | 40 | 25 |
| Comp. Ex. 49 | 20-150 | 20-150 | 5 | 25 | 40 | 30 | 25 | 10 | 5 |
| Comp. Ex. 50 | 100-350 | 20-150 | 10 | 25 | 35 | 35 | 25 | 15 | 5 |
| Comp. Ex. 51 | 20-50 | 100-250 | 0 | 5 | 10 | 5 | 0 | 0 | 0 |
| Comp. Ex. 52 | 10-50 | 100-250 | 5 | 15 | 10 | 5 | 5 | 0 | 0 |
| Comp. Ex. 53 | 150-250 | 100-250 | 5 | 25 | 30 | 25 | 10 | 5 | 0 |
| Comp. Ex. 54 | 20-150 | — | 5 | 25 | 40 | 20 | 10 | 0 | 0 |

Examples 64 and 65 and Comparative Examples 55 to 57

To 10 mg of leuprolide (produced by Bachem Co.), one of luteinizing hormone-releasing hormones, 160 mg of microcrystalline cellulose (Avicel PH101 produced by Asahi Kasei Co.) whose average particle diameters in at least 90 wt % based on the particles had been adjusted to 50-350 µm and 40 mg of hydroxypropyl cellulose (HPC-H produced by Nippon Soda Co.) whose particle diameters in at least 90 wt % based on the particles had been adjusted to 10-100 µm were added and mixed. Subsequently, 0.21 mg of magnesium stearate as a lubricant was added to the mixture to prepare a powdery composition (Examples 64 and 65 and Comparative Examples 55 to 57). Hydroxypropyl cellulose used here had a viscosity of 2.0-2.9 cps (Comparative Example 55), 3.0-5.9 cps (Comparative Example 56), 6.0-10.0 (Comparative Example 57), 150-400 cps (Example 64) and 1000-4000 cps (Example 65), all in a 2% aqueous solution.

Each of the compositions (Examples 64 and 65 and Comparative Examples 55 to 57) was administered into the nasal cavity of a male Japanese white rabbit (weighing 2.5-3.0 kg) with a powder sprayer (Puvlizer® made by Teijin Co.) so that the dose of the composition became 2.5 mg/kg. The blood samples were withdrawn from the ear vein periodically after the administration, and leuprolide levels in blood were determined by RIA. The results are shown in Table 11. It is clear that when the viscosity of hydroxypropyl cellulose was 150 cps or more, the absorption of the drug was extremely improved and maximum blood concentrations were highly increased.

Examples 66 and Comparative Examples 58 to 60

To 10 mg of a hydrophilic polysaccharide FITC-dextran (produced by Sigma Co.; average molecular weight of 4400), a model compound of a peptide/proteinaceous drug, hydroxypropyl cellulose (HPC produced by Nippon Soda Co.) and microcrystalline cellulose (Avicel PH101 produced by Asahi Kasei Co.) in amounts of 19 mg and 171 mg, respectively, both of which had average particle diameters shown in Table 12 in at least 90 wt % based on the particles were added and mixed to prepare powdery compositions (Example 66 and Comparative Example 58 and 59), or only microcrystalline cellulose (Avicel PH101 produced by Asahi Kasei Co.) in an amount of 190 mg was added and mixed (Comparative Example 60).

Figure 1:
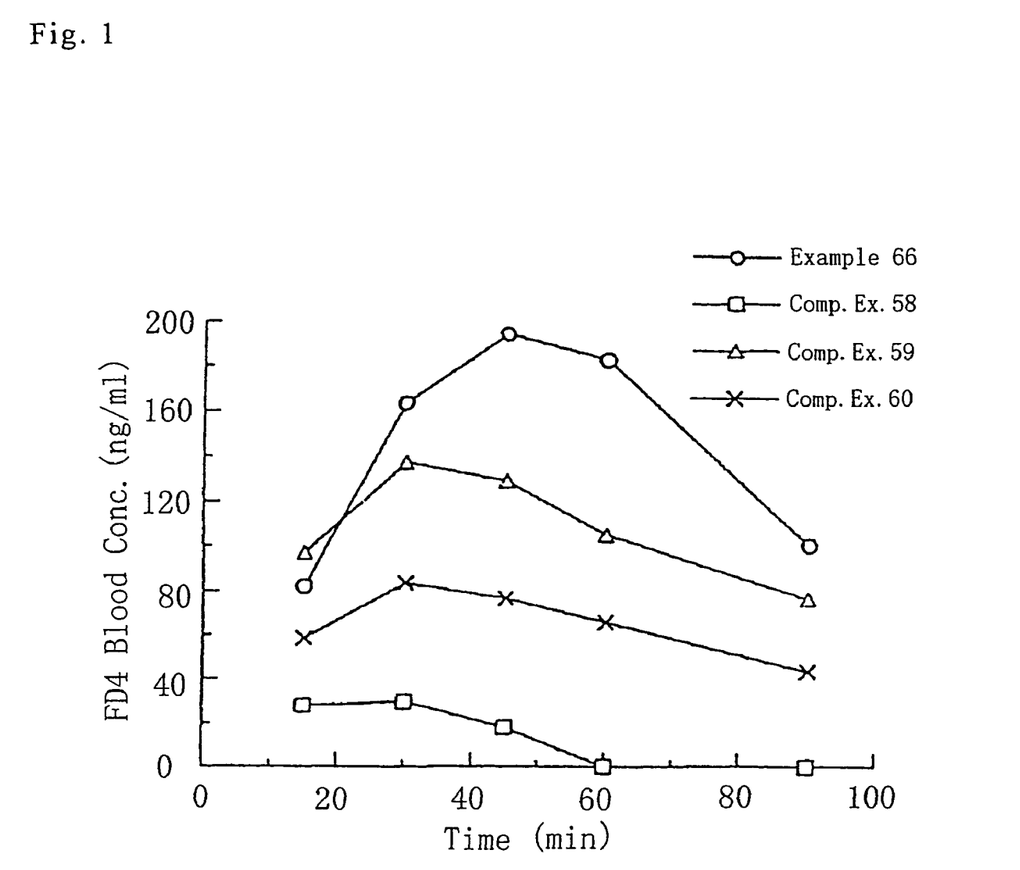
FIG. 1 shows FITC-dextran (FD4) concentrations (ng/ml) when a powdery composition for nasal administration having an improved absorption of the present invention (Example 66: -○-) and powdery compositions for nasal administration of Comparative Examples (Comparative Examples 58, 59 and 60: -□-, -Δ- and -X-, respectively) were administered to rabbits.

Each of the compositions was administered into the nasal cavity of a male Japanese white rabbit (weighing 3.0 kg) with a powder sprayer (Puvlizer® made by Teijin Co.) so that the dose of the composition became 4 mg/kg. The blood samples were withdrawn from the ear vein periodically after the administration, and FITC-dextran (FD4) levels in blood (ng/ml) were determined by HPLC, and the results are shown in FIG. 1.

It is clear from the FIGURE that the combination of microcrystalline cellulose, a water-absorbing and water-insoluble base material, with hydroxypropyl cellulose, a water-absorbing and gel-forming base material, in an amount of 11 wt % based on the microcrystalline cellulose, improved maximum blood concentrations from single use of microcrystalline cellulose as a base material component and that a composition of the present invention, in which the average particle diameter

TABLE 11

Time Course of Blood Concentration of Leuprolide after Administration of Each Composition

|  | viscosity* of HPC (cps) | 15 min | 30 min | 45 min | 60 min | 90 min | 120 min | (ng/ml) 180 min |
|---|---|---|---|---|---|---|---|---|
| Example 64 | 150-400 | 70 | 100 | 130 | 95 | 70 | 50 | 20 |
| Example 65 | 1000-4000 | 60 | 120 | 130 | 100 | 65 | 45 | 15 |
| Comp. Ex. 55 | 2.0-2.9 | 35 | 60 | 50 | 40 | 40 | 20 | 10 |
| Comp. Ex. 56 | 3.0-5.9 | 40 | 65 | 50 | 45 | 30 | 25 | 20 |
| Comp. Ex. 57 | 6.0-10.0 | 35 | 35 | 50 | 40 | 40 | 35 | 25 |

*viscosity of 2% aqueous solution of the hydroxypropyl cellulose was 38-50 μm, further significantly increased the maximum blood concentration.

TABLE 12

Range of Particle Diameters in 90 wt %
or More of Particles of Each Base material

|  | CC | HPC (μm) |
|---|---|---|
| Example 66 | 38-150 | 38-50 |
| Comp. Ex. 58 | 38-150 | 38-150 |
| Comp. Ex. 59 | 38-150 | 150-350 |
| Comp. Ex. 60 | 38-150 | — |

Examples 67 and 68 and Comparative Examples 61 to 63

To 5 mg of 5-carboxyfluorescein (produced by Sigma Co.; molecular weight of 376.3) as a model compound of a low molecular drug, hydroxypropyl cellulose (HPC produced by Nippon Soda Co.) and microcrystalline cellulose (Avicel PH101 produced by Asahi Kasei Co.) in amounts of 100 mg and 400 mg, respectively, both of which had average particle diameters shown in Table 13 in at least 90 wt % based on the particles, were added to prepare powdery compositions (Examples 67 and 68 and Comparative Example 61 to 63).

Each of the compositions was administered into the nasal cavity of a male Japanese white rabbit (weighing 2.5) with a powder sprayer (Puvlizer® made by Teijin Co.) so that the dose of the composition became 2.5 mg/kg. The blood samples were withdrawn from the ear vein periodically after the administration, and 5-carboxyfluorescein levels in blood were determined by HPLC. The results are shown in Table 13.

Table 13 shows that compositions of the present invention exhibited significant improvement in blood concentrations of the compound.

and they were mixed by a ball mill (Example 69). Into 100 ml of water, 0.1 mg of salmon calcitonin and 120 mg of microcrystalline cellulose were added to disperse them, and dispersion was freeze dried. The obtained solid was pulverized in a mortar, and the pulverized matter was sieved so that at least 90 wt % based on the particles had an average particle diameter of 10-350 μm, and 30 mg of hydroxypropyl cellulose was added to the resultant fraction of particles in a mortar, and they were mixed (Example 70). In a ball mill, 0.10 mg of salmon calcitonin, 120 mg of microcrystalline cellulose and 30 mg of hydroxypropyl cellulose were mixed by one step (Example 71). In a mortar, 0.1 mg of salmon calcitonin and 30 mg of hydroxypropyl cellulose were mixed, subsequently 120 mg of crystalline cellulose was added to the resultant mixture, and they were mixed by a ball mill (Comparative Example 64). Into 100 ml of water, 0.10 mg of salmon calcitonin and 30 mg of hydroxypropyl cellulose were dissolved, and the solution was freeze dried. The obtained solid was pulverized in a mortar, and the resultant particles were sieved to obtain a fraction having an average particle diameter of 10-350 μm in at least 90 wt % based on the particles. Then, 120 mg of fine cellulose was added to the fraction of the particles, and they were mixed in a ball mill (Comparative Example 65).

Each of the compositions (Examples 69 to 71 and Comparative Examples 64 and 65) prepared by these processes was administered into the nasal cavity of a male Japanese white rabbit (weighing 2.5-3.0 kg) with a powder sprayer (Puvlizer® made by Teijin Co.) so that the dose of the composition became 0.6 mg/kg. The blood samples were withdrawn from the ear vein periodically after the administration, and salmon calcitonin levels in blood were determined by RIA, and the results are shown in Table 14. It is clear from Table 14 that when compositions of the present invention (Examples 69 to 71) were administered, extreme increases in maximum blood concentrations were observed, while when compositions of Comparative Examples 64 and 65 were administered, such extreme increases were not observed.

TABLE 13

Time Course of Blood Concentration of 5-Carboxyfluorescein after Administration of Each Composition

|  | CC | HPC | 5 min | 15 min | 30 min | 45 min | 60 min | 90 min (ng/ml) |
|---|---|---|---|---|---|---|---|---|
| Example 67 | 38-150 | 38-63 | 8.6 | 13.8 | 12.1 | 9.4 | 6.6 | 4.3 |
| Example 68 | 38-150 | 63-105 | 10.7 | 14.7 | 15.7 | 10.0 | 8.3 | 6.3 |
| Comp. Ex. 61 | 38-150 | 38-150 | 11.3 | 9.7 | 8.1 | 6.0 | 4.4 | 4.0 |
| Comp. Ex. 62 | 38-150 | 105-150 | 6.6 | 6.5 | 6.5 | 5.5 | 4.4 | 2.7 |
| Comp. Ex. 63 | 38-150 | 150-250 |  | 3.1 | 5.7 | 6.0 | 3.7 | 2.6 |

Examples 69 to 71 and Comparative Examples 64 and 65

Compositions (Examples 69 to 71 and Comparative Examples 64 and 65) were prepared by the following processes using salmon calcitonin (produced by Bachem Co.), one of calcitonins, microcrystalline cellulose (Avicel PH101 produced by Asahi Kasei Co.) whose average particle diameter had been adjusted to 10-350 μm in at least 90 wt % based on the particles and hydroxypropyl cellulose (HPC produced by Nippon Soda Co.) whose average particle diameter had been adjusted to 10-350 μm in at least 90 wt % based on the particles.

In a mortar, 0.10 mg of salmon calcitonin and 120 mg of the microcrystalline cellulose were mixed beforehand, 30 mg of hydroxypropyl cellulose were added to the resultant mixture,

TABLE 14

Time Course of Blood Concentration of Salmon Calcitonin after Administration of Each Composition

|  | 15 min | 30 min | 45 min | 60 min | 90 min | 120 min | 180 min (pg/ml) |
|---|---|---|---|---|---|---|---|
| Example 69 | 30 | 70 | 75 | 65 | 55 | 35 | 20 |
| Example 70 | 30 | 75 | 85 | 75 | 65 | 55 | 40 |
| Example 71 | 25 | 55 | 60 | 45 | 35 | 25 | 15 |
| Comp. Ex. 64 | 5 | 25 | 40 | 30 | 25 | 10 | 5 |
| Comp. Ex. 65 | 5 | 15 | 20 | 10 | 5 | 0 | 0 |

Examples 72 to 74 and Comparative Examples 66 and 67

Powdery compositions (Examples 72 to 74 and Comparative Examples 66 and 67) were prepared by the following processes using 5-carboxyfluorescein (produced by Sigma Co.) as a model compound of a lower molecular drug, microcrystalline cellulose (Avicel PH1101 produced by Asahi Kasei Co.) whose average particle diameter had been adjusted to 10-150 μm in at least 90 wt % based on the particles and hydroxypropyl cellulose (HPC-H produced by Nippon Soda Co.) whose average particle diameters had been adjusted to 10-350 μm in at least 90 wt % based on the particles.

Five mg of 5-carboxyfluorescein, 350 mg of microcrystalline cellulose and 150 mg of hydroxypropyl cellulose were weighed out and they were mixed by a high-speed mixer by one step (Example 72). Five mg of 5-carboxyfluorescein and 350 mg of microcrystalline cellulose were weighed into a mortar and mixed, subsequently 150 mg of hydroxypropyl cellulose was added to the resultant mixture, and they were mixed by a cross-rotary mixer (Example 73). Into 10 ml of purified water, 5 mg of 5-carboxyfluorescein and 350 mg of microcrystalline cellulose were dissolved or dispersed, and the resultant solution or dispersion was freeze dried. The obtained cake was pulverized and the resultant powder was sieved to obtain a fraction of particles having an average particle diameter of 10-350 μm. From the particles of the obtained fraction, 280 mg was weighed, and 120 mg of hydroxypropyl cellulose was added to it and they were mixed by a ball-free ball mill (Example 74).

Five mg of 5-carboxyfluorescein, 350 mg of microcrystalline cellulose and 150 mg of hydroxypropyl cellulose were each weighed out and they were mixed by a ball-free ball mill by one step (Comparative Example 66). Into 10 ml of purified water, 5 mg of 5-carboxyfluorescein and 150 mg of hydroxypropyl cellulose were dissolved or dispersed, and the resultant solution or dispersion was freeze dried. The obtained cake was pulverized and the obtained powder was sieved to obtain a fraction of particles having an average particle diameter of 10-350 μm. From the particles of the obtained fraction, 90 mg was weighed out, and 210 mg of microcrystalline cellulose was added to it, and they were mixed by a ball-free ball mill (Comparative Example 67).

Each of the compositions prepared by these processes was administered into the nasal cavity of a male Japanese white rabbit (weighing 2.5 kg) with a powder sprayer (Puvlizer® made by Teijin Co.) so that the dose of the composition became 7.5 mg/kg. The blood samples were withdrawn from the ear vein periodically after the administration, and 5-carboxyfluorescein levels in blood were determined by HPLC. The results are shown in Table 15. It is clear from Table 15 that when compositions of the present invention (Examples 72 to 74) were administered, extreme increases in maximum blood concentrations comparing the compositions of the Comparative Examples were observed.

TABLE 15

Time Course of Blood Concentration of 5-Carboxyfluorescein after Administration of Each Composition

|  | 15 min | 30 min | 45 min | 60 min | (ng/ml) 90 min |
|---|---|---|---|---|---|
| Example 72 | 12.9 | 8.5 | 6.1 | 4.1 | 2.2 |
| Example 73 | 10.3 | 9.8 | 9.0 | 8.2 | 5.6 |
| Example 74 | 10.7 | 8.3 | 6.2 | 4.6 | 2.7 |

TABLE 15-continued

Time Course of Blood Concentration of 5-Carboxyfluorescein after Administration of Each Composition

|  | 15 min | 30 min | 45 min | 60 min | (ng/ml) 90 min |
|---|---|---|---|---|---|
| Comp. Ex. 66 | 5.1 | 4.8 | 3.8 | 3.0 | 2.1 |
| Comp. Ex. 67 | 3.5 | 4.0 | 4.2 | 3.5 | 2.2 |

Examples 75 to 77 and Comparative Examples 68 and 69

Powdery compositions (Examples 75 to 77 and Comparative Examples 68 and 69) were prepared by the following processes using fluorescein (produced by Wako Junyaku Co.), i.e. a model compound of a lipophilic lower molecular drug, microcrystalline cellulose (Avicel PH101 produced by Asahi Kasei Co.) whose average particle diameter had been adjusted to 10-350 μm in at least 90 wt % based on the particles and hydroxypropyl cellulose (HPC-H produced by Nippon Soda Co.) whose average particle diameters had been adjusted to 10-350 μm in at least 90 wt % based on the particles.

Five mg of fluorescein, 400 mg of microcrystalline cellulose and 100 mg of hydroxypropyl cellulose were weighed out, and they were mixed by a powerful auto mixer by one step (Example 75). In a mortar, 5 mg of fluorescein and 400 mg of microcrystalline cellulose were mixed, subsequently 100 mg of hydroxypropyl cellulose was added to the resultant mixture, and they were mixed by a ball-free ball mixer (Example 76). Into 10 ml of ethanol, 5 mg of fluorescein and 400 mg of microcrystalline cellulose were dissolved or dispersed, and the solvent was evaporated to dry up. The obtained powder was pulverized again and the resultant particles were sieved to obtain a fraction of particles having an average particle diameters of 10-350 μm. From the particles of the obtained fraction, 320 mg was weighed out, and subsequently 80 mg of hydroxypropyl cellulose was added to it, and they were mixed by a ball-free ball mill (Example 77).

Five mg of fluorescein, 400 mg of microcrystalline cellulose and 100 mg of hydroxypropyl cellulose were each weighed out and they were mixed by one step by a ball-free ball mill (Comparative Example 68). Into 10 ml of ethanol, 5 mg of fluorescein and 100 mg of hydroxypropyl cellulose were dissolved or dispersed, and the solvent was evaporated to dry up. The obtained film was pulverized and the resultant powder was sieved to obtain a fraction of particles having an average particle diameter of 10-350 μm. From the particles of the obtained fraction, 80 mg was weighed out, and subsequently 320 mg of microcrystalline cellulose was added to it, and they were mixed by a ball-free ball mill (Comparative Example 69).

Each of the compositions prepared by these processes was administered into the nasal cavity of a male Japanese white rabbit (weighing 2.5 kg) with a powder sprayer (Puvlizer® made by Teijin Co.) so that the dose of the composition became 7.5 mg/kg. The blood samples were withdrawn from the ear vein periodically after the administration, and fluorescein levels in blood were determined by HPLC. The results are shown in Table 16. It is clear from Table 16 that when compositions of the present invention (Examples 75 to 77) were administered, extreme increases in blood concentrations comparing the compositions of the Comparative Examples were observed.

TABLE 16

Time Course of Blood Concentration of Fluorescein after Administration of Each Composition

|  | 15 min | 30 min | 45 min | 60 min | 90 min (ng/ml) |
|---|---|---|---|---|---|
| Example 75 | 11.2 | 8.5 | 7.1 | 4.8 | 3.2 |
| Example 76 | 12.3 | 9.8 | 9.0 | 8.2 | 5.6 |
| Example 77 | 15.7 | 18.3 | 13.2 | 8.6 | 5.7 |
| Comp. Ex. 68 | 7.1 | 5.8 | 4.3 | 3.5 | 2.8 |
| Comp. Ex. 69 | 2.8 | 3.6 | 3.6 | 3.0 | 1.8 |

What is claimed is:

1. A powdery composition for nasal administration comprising
(i) a drug,
(ii) one or more of a water-absorbing and gel-forming base material selected from the group consisting of hydroxypropyl cellulose, hydroxypropylmethyl cellulose, methyl cellulose, hydroxyethyl cellulose, and sodium carboxymethyl cellulose and
(iii) one or more of a water-absorbing and water-insoluble base material selected from the group consisting of crystalline cellulose, α-cellulose, cross-linked sodium carboxy-methyl cellulose, cross-linked starch, chitin and chitosan,
wherein the content of the water-absorbing and gel-forming base material is about 5-40 wt % based on the total of the water-absorbing and water-insoluble base material and the water-absorbing and gel-forming base material,
70 wt % or more based on the drug is dispersed on or in the water-absorbing and water-insoluble base material and on or in the water-absorbing and gel-forming base material,
the water-absorbing and water-insoluble base material and water-absorbing and gel-forming base material comprise particles,
wherein the drug is dispersed more on or in the water-absorbing and water-insoluble base material than in a state in which the drug is adhered to the both base materials according to their compounding ratio, and
wherein the powdery composition is obtained by a method comprising mechanically mixing the drug with the water-absorbing and water-insoluble base material to obtain a resultant mixture, in which at least 90 wt % based on the water-absorbing and water-insoluble particles have an average particle diameter in the range of 10-350 pm, using a universal mixer, a ribbon mixer, an automatic mortar, a ball mill, a high-speed mixer or a powerful automatic mixer, and subsequently, mechanically mixing the water-absorbing and gel-forming base material, in which at least 90 wt % based on the water-absorbing and gel-forming particles have an average particle diameter in the range of 10-350 μm, with the resultant mixture.

2. A powdery composition for nasal administration according to claim 1, wherein the drug is selected from the group consisting of non-peptide/non-proteinaceous drugs and peptide/proteinaceous drugs having molecular weight of 30,000 or less.

3. A powdery composition for nasal administration according to claim 2, wherein the non-peptide/non-proteinaceous drug is one or more drugs selected from the group consisting of anti-inflammatory steroids, nonsteroidal anti-inflammatory drugs, analgesic anti-inflammatory agents, antitussive expectorants, antihistaminic agents, antiallergic drugs, antiemetic drugs, hypnotics, vitamin preparations, sex steroid hormones, antineoplastic drugs, antiarrhythmic drugs, antihypertensive drugs, antianxiety drugs, psychotropic drugs, antiulcer drugs, cardiotonics, analgesics, bronchodilators, treating agents for obesity, antithrombotic drugs, antidiabetic drugs, muscle relaxants and anti-rheumatics.

4. A powdery composition for nasal administration according to claim 2, wherein the peptide/proteinaceous drug is one or more drugs selected from the group consisting of luteinizing hormone-releasing hormones, growth hormone-releasing factors, somatostatins, vasopressins, oxytocins, hirudins, enkephalins, adrenocorticotropic hormones, bradykinins, calcitonins, insulins, glucagons, growth hormones, growth hormone-releasing hormones, luteinizing hormones, insulin-like growth factors, calcitonin, gene-related peptides, atrial natriuretic polypeptides, interferons, erythropoietin, granulocyte, colony forming-stimulating factor, macrophage forming-stimulating factor, parathyroid hormones, parathyroid hormone-releasing hormone, prolactin, thyroid-stimulating hormone-releasing hormone and angiotensins.

5. A powdery composition for nasal administration according to claim 1, wherein the drug is a peptide/proteinaceous drug having a molecular weight of 500-1500, and the amount of the water-absorbing and gel-forming base material is about 5-30 wt % based on the total of the water-absorbing and water-insoluble base material and the water-absorbing and gel-forming base material.

6. A powdery composition for nasal administration according to claim 5, wherein the peptide/proteinaceous drug is one or more drugs selected from the group consisting of vasopressins, luteinizing hormone-releasing hormones, growth hormone-releasing factors, somatostatins, oxytocins, hirudins, enkephalins, adrenocorticotropic hormones and bradykinins.

7. A powdery composition for nasal administration according to claim 1, wherein the drug is a peptide/proteinaceous drug having a molecular weight of 1500-30,000 and the amount of the water-absorbing and gel-forming base material is about 5-20 wt % based on the total of the water-absorbing and water-insoluble base material and the water-absorbing and gel-forming base material.

8. A powdery composition for nasal administration according to claim 7, wherein the peptide/proteinaceous drug is one or more drugs selected from the group consisting of calcitonins, insulins, glucagons, growth hormones, growth hormone-releasing hormones, luteinizing hormones, insulin-like growth factors, calcitonin gene-related peptides, atrial natriuretic polypeptides, interferons, erythropoietin, granulocyte colony-stimulating factor, macrophage-stimulating factor, parathyroid hormones, parathyroid hormone-releasing hormone, prolactin, thyroid-stimulating hormone-releasing hormone and angiotensins.

9. A powdery composition for nasal administration according to claim 1, wherein the water-absorbing and water-insoluble base material is crystalline cellulose.

10. A powdery composition for nasal administration according to claim 1, wherein the water-absorbing and gel-forming base material is hydroxypropyl cellulose.

11. A powdery composition for nasal administration according to claim 10, wherein the hydroxypropyl cellulose has a viscosity of 150-4000 cps in 2% aqueous solution.

12. A powdery composition for nasal administration comprising
(i) a drug,
(ii) one or more of a water-absorbing and gel-forming base material selected from the group consisting of hydroxypropyl cellulose, hydroxypropylmethyl cellulose, methyl cellulose, hydroxyethyl cellulose, and sodium carboxymethyl cellulose and (iii) one or more of a water-absorbing and water-insoluble base material selected from the group consisting of crystalline cellulose, α-cellulose, cross-linked sodium carboxy-methyl cellulose, cross-linked starch, chitin and chitosan, wherein the content of the water-absorbing and gel-forming base material is about 5-40 wt % based on the total of the water-absorbing and water-insoluble base material and the water-absorbing and gel-forming base material, 70 wt % or more based on the drug is dispersed on or in the water-absorbing and water-insoluble base material and on or in the water-absorbing and gel-forming base material, the water-absorbing and water-insoluble base material and water-absorbing and gel-forming base material comprise particles, wherein the drug is dispersed more on or in the water-absorbing and water-insoluble base material than in a state in which the drug is adhered to the both base materials according to their compounding ratio, and wherein the powdery composition is obtained by a method comprising dissolving or dispersing the drug and the water-absorbing and water-insoluble base material in an organic solvent to obtain a resultant solution or dispersion, and subsequently evaporating the resultant solution or dispersion to obtain a powder, further pulverizing and sieving the powder to obtain a resultant powder comprising water-absorbing and water-insoluble particles, wherein at least 90 wt % based on the water absorbing and water-insoluble particles have an average particle diameter in the range of 10-350 pm, and mechanically mixing the water-absorbing and gel-forming base material, in which at least 90 wt % based on the water-absorbing and gel-forming particles have an average particle diameter in the range of 10-350 µm, with the resultant powder.

13. A powdery composition for nasal administration according to claim 12, wherein the drug is selected from the group consisting of non-peptide/non-proteinaceous drugs and peptide/proteinaceous drugs having molecular weight of 30,000 or less.

14. A powdery composition for nasal administration according to claim 13, wherein the non-peptide/non-proteinaceous drug is one or more drugs selected from the group consisting of anti-inflammatory steroids, nonsteroidal anti-inflammatory drugs, analgesic anti-inflammatory agents, antitussive expectorants, antihistaminic agents, antiallergic drugs, antiemetic drugs, hypnotics, vitamin preparations, sex steroid hormones, antineoplastic drugs, antiarrhythmic drugs, antihypertensive drugs, antianxiety drugs, psychotropic drugs, antiulcer drugs, cardiotonics, analgesics, bronchodilators, treating agents for obesity, antithrombotic drugs, antidiabetic drugs, muscle relaxants and anti-rheumatics.

15. A powdery composition for nasal administration according to claim 13, wherein the peptide/proteinaceous drug is one or more drugs selected from the group consisting of luteinizing hormone-releasing hormones, growth hormone-releasing factors, somatostatins, vasopressins, oxytocins, hirudins, enkephalins, adrenocorticotropic hormones, bradykinins, calcitonins, insulins, glucagons, growth hormones, growth hormone-releasing hormones, luteinizing hormones, insulin-like growth factors, calcitonin gene-related peptides, atrial natriuretic polypeptides, interferons, erythropoietin, granulocyte colony forming-stimulating factor, macrophage forming-stimulating factor, parathyroid hormones, parathyroid hormone-releasing hormone, prolactin, thyroid-stimulating hormone-releasing hormone and angiotensins.

16. A powdery composition for nasal administration according to claim 12, wherein the drug is a peptide/proteinaceous drug having a molecular weight of 500-1500, and the amount of the water-absorbing and gel-forming base material is about 5-30 wt % based on the total of the water-absorbing and water-insoluble base material and the water-absorbing and gel-forming base material.

17. A powdery composition for nasal administration according to claim 16, wherein the peptide/proteinaceous drug is one or more drugs selected from the group consisting of vasopressins, luteinizing hormone-releasing hormones, growth hormone-releasing factors, somatostatins, oxytocins, hirudins, enkephalins, adrenocorticotropic hormones and bradykinins.

18. A powdery composition for nasal administration according to claim 12, wherein the drug is a peptide/proteinaceous drug having a molecular weight of 1500-30,000 and the amount of the water-absorbing and gel-forming base material is about 5-20 wt % based on the total of the water-absorbing and water-insoluble base material and the water-absorbing and gel-forming base material.

19. A powdery composition for nasal administration according to claim 18, wherein the peptide/proteinaceous drug is one or more drugs selected from the group consisting of calcitonins, insulins, glucagons, growth hormones, growth hormone-releasing hormones, luteinizing hormones, insulin-like growth factors, calcitonin gene-related peptides, atrial natriuretic polypeptides, interferons, erythropoietin, granulocyte colony-stimulating factor, macrophage-stimulating factor, parathyroid hormones, parathyroid hormone-releasing hormone, prolactin, thyroid-stimulating hormone-releasing hormone and angiotensins.

20. A powdery composition for nasal administration according to claim 12, wherein the water-absorbing and water-insoluble base material is crystalline cellulose.

21. A powdery composition for nasal administration according to claim 12, wherein the water-absorbing and gel-forming base material is hydroxypropyl cellulose.

22. A powdery composition for nasal administration according to claim 21, wherein the hydroxypropyl cellulose has a viscosity of 150-4000 cps in 2% aqueous solution.

* * * * *